US010059650B2

(12) United States Patent
Barta et al.

(10) Patent No.: US 10,059,650 B2
(45) Date of Patent: Aug. 28, 2018

(54) SYSTEMS AND METHODS FOR THE DEPOLYMERIZATION OF A BIOPOLYMER

(71) Applicant: Yale University, New Haven, CT (US)

(72) Inventors: Katalin Barta, Groningen (NL); Paul Anastas, Guilford, CT (US); Evan Beach, Wallingford, CT (US); Thomas Hansen, Kalundborg (DK); Genoa Warner, Pittsburgh, PA (US); Patrick Foley, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/897,306

(22) PCT Filed: Jun. 13, 2014

(86) PCT No.: PCT/US2014/042263
§ 371 (c)(1),
(2) Date: Dec. 10, 2015

(87) PCT Pub. No.: WO2014/201325
PCT Pub. Date: Dec. 18, 2014

(65) Prior Publication Data
US 2016/0130202 A1    May 12, 2016

Related U.S. Application Data

(60) Provisional application No. 61/835,140, filed on Jun. 14, 2013, provisional application No. 61/872,263, filed on Aug. 30, 2013, provisional application No. 61/890,535, filed on Oct. 14, 2013.

(51) Int. Cl.
| | | |
|---|---|---|
| C07C 37/54 | (2006.01) |
| C07C 51/09 | (2006.01) |
| B01J 21/10 | (2006.01) |
| B01J 23/00 | (2006.01) |
| B01J 23/10 | (2006.01) |
| B01J 23/26 | (2006.01) |
| B01J 23/34 | (2006.01) |
| B01J 23/72 | (2006.01) |
| C08H 7/00 | (2011.01) |

(52) U.S. Cl.
CPC ............... *C07C 37/54* (2013.01); *B01J 21/10* (2013.01); *B01J 23/002* (2013.01); *B01J 23/10* (2013.01); *B01J 23/26* (2013.01); *B01J 23/34* (2013.01); *B01J 23/72* (2013.01); *C07C 51/09* (2013.01); *C08H 6/00* (2013.01); *B01J 2523/00* (2013.01)

(58) Field of Classification Search
CPC ...................................................... C07C 37/54
See application file for complete search history.

(56) References Cited

U.S. PATENT DOCUMENTS

| | | | |
|---|---|---|---|
| 3,689,540 A | | 9/1972 | James et al. |
| 5,807,952 A | * | 9/1998 | Agblevor ............... C07B 41/02 527/400 |
| 5,959,167 A | * | 9/1999 | Shabtai ................. C10G 1/002 585/240 |
| 6,214,976 B1 | * | 4/2001 | Watanabe ............... C08H 6/00 530/500 |
| 2003/0216326 A1 | | 11/2003 | Alimi |
| 2008/0050792 A1 | * | 2/2008 | Zmierczak ............ C10G 1/002 435/161 |
| 2011/0005697 A1 | | 1/2011 | Shoseyov |
| 2011/0306804 A1 | | 12/2011 | Cortright |
| 2012/0289692 A1 | | 11/2012 | Gray et al. |
| 2012/0302796 A1 | * | 11/2012 | Dhepe ................... C07C 37/004 568/309 |
| 2013/0066116 A1 | * | 3/2013 | Goettmann .............. C07G 1/00 568/652 |
| 2013/0150630 A1 | * | 6/2013 | Liu ......................... C07C 37/50 568/799 |
| 2013/0232853 A1 | * | 9/2013 | Peterson ................. C07G 1/00 44/307 |
| 2014/0096830 A1 | * | 4/2014 | Gastaldo ................ C07C 37/54 137/1 |
| 2014/0107381 A1 | * | 4/2014 | Beckham ............... B01J 37/031 585/240 |
| 2014/0249300 A1 | * | 9/2014 | Bozell ...................... C07G 1/00 530/507 |
| 2014/0335571 A1 | * | 11/2014 | Chen-Sarkanen ...... C12P 19/00 435/99 |
| 2015/0065339 A1 | * | 3/2015 | Bloomfield ............ C07C 45/28 502/155 |
| 2015/0218073 A1 | * | 8/2015 | Samec .................... C07G 1/00 568/426 |

(Continued)

FOREIGN PATENT DOCUMENTS

WO         2012151242         8/2012

OTHER PUBLICATIONS

Macala et al., ChemSusChem, Feb. 2009, 215-217.*

(Continued)

*Primary Examiner* — Liam J Heincer
(74) *Attorney, Agent, or Firm* — Riverside Law LLP

(57) ABSTRACT

Methods for the production and isolation of a monomer from a biopolymer are described. The method includes extracting a biopolymer from a biopolymer source and depolymerizing the biopolymer into a monomer.

Methods for the production and isolation of a monomer from corn lignin are also described. The method includes extracting corn lignin from corn biomass and depolymerizing the corn lignin into a monomer.

12 Claims, 31 Drawing Sheets

(56) References Cited

U.S. PATENT DOCUMENTS

2015/0337214 A1* 11/2015 Murray .................. C10G 3/45
585/357
2016/0152648 A1* 6/2016 Bloomfield ............ C07C 45/28
205/343

OTHER PUBLICATIONS

Chesson et al., "Influence of Plant Phenolic Acids on Growth and Cellulolytic Activity of Rumen Bacteria." 1982, Applied and Environmental Microbiology. 44(3):597-603.

Zakzeski et al., "The Catalytic Valorization of Lignin for the Production of Renewable Chemicals." 2010, Chem. Rev. 110:3552-3599.

Kobayashi et al., "Conversion of lignocellulose into renewable chemicals by heterogenous catalysis." 2012, Catalysis Science & Technology 2:869-883.

Torr et al., "Mild hydrogenolysis of in-situ and isolated pinus radiate lignins." 2011, Bioresource Technol. 102:7608-7611.

Ye et al., "Selective production of 4-ethylphenolics from lignin via mild hydrogenolysis." 2012, Bioresour. Technol. 118:648-651.

Song et al., "Lignin depolymerization (LDP) in alcohol over nickel-based catalysts via a fragmentation-hydrogenolysis process." 2013, Energy Environ. Sci. 6:994-1007.

Wang and Rinaldi, "Solvent Effects on the Hydrogenolysis of Diphenyl Ether with Raney Nickel and their Implications for the Conversion of Lignin." 2012, ChemSusChem 5:1455-1466.

He et al., "Ni-Catalyzed Cleavage of Aryl Ethers in the Aqueous Phase." 2012, J. Am. Chem. Soc. 134:20768-20775.

Matson et al., "One-Pot Catalytic Conversion of Cellulose and of Woody Biomass Solids to Liquid Fuels." 2011, J. Am. Chem. Soc. 133:14090-14097.

Klein et al., "Accelerated Solvent Extraction of Lignin from *Aleurites moluccana* (Candlenut) Nutshells." 2010, J. Agric. Food Chem. 58:10045-10048.

Roberts et al., "Towards Quantitative Catalytic Lignin Depolymerization." 2011, Chem. Eur. J. 17:5939-5948.

Barta et al. "Catalytic disassembly of an organosolv lignin via hydrogen transfer from supercritical methanol" 2010, Green Chem., 12, 1640-1647.

* cited by examiner

SYSTEMS AND METHODS FOR THE DEPOLYMERIZATION OF A BIOPOLYMER

CROSS-REFERENCE TO RELATED APPLICATIONS

This present application is a PCT patent application claiming priority to U.S. Provisional Application No. 61/835,140, filed on Jun. 14, 2013, U.S. Provisional Application No. 61/872,263, filed on Aug. 30, 2013, and U.S. Provisional Application No. 61/890,535, filed on Oct. 14, 2013, which applications are each incorporated by reference herein in their entireties.

STATEMENT REGARDING FEDERALLY SPONSORED RESEARCH OR DEVELOPMENT

This invention was made with government support under 2010-38202-21853 awarded by the United States Department of Agriculture (USDA). The government has certain rights in the invention.

BACKGROUND OF THE INVENTION

Efficient depolymerization of biopolymers derived from renewable resources represents a great challenge for modern chemistry due to the complexity of starting materials as well as product mixtures generated. It requires specially tailored reaction conditions and catalysts capable of selective bond cleavage reactions. Aromatics are an important target compound group since they incorporate valuable structural features for a variety of industrial applications.

Conventional approaches for lignin depolymerization include pyrolysis and liquefaction techniques. However, most pyrolysis and liquefaction methods mainly result in complex mixtures rather than well-defined aromatics (Zakzeski et al., 2010, Chem. Rev. 110:3552-3599; Pandey et al., 2012, Catalysis Science & Technology, 2:869-883; Huber et al., 2006, Chem. Rev. 106:4044-4098). Recently, a number of promising systems have been developed for the more controlled depolymerization of lignin. Lercher and coworkers described base catalyzed mild depolymerization of lignin to aromatics with high yield, and have shown that the composition of the product mixture strongly depended on reaction conditions (Roberts et al., 2011, Chem. Eur. J. 17:5939-5948). Catalytic hydrogenolysis of ethanol soluble lignin using was described by Ragauskas and coworkers (Nagy et al., 2009, Holzforschung 63:513-520). Efficient hydrogenolysis of in situ and isolated lignins was reported by Torr and coworkers using palladium on carbon resulting in good yields of biooils that mainly contained aromatic monomers and dimers (Torr et al., 2011, Bioresour. Technol. 102:7608-7611). Chang described the selective production of 4-ethylphenolics via mild hydrogenolysis, albeit with moderate product yields (Ye et al., 2012, Bioresour. Technol. 118:648-651). Depolymerization and hydrodeoxygenation of switch grass lignin with formic acid was described by Jones (Xu et al., 2012, ChemSusChem 5:667-675). Lignin depolymerization using earth-abundant metal-based catalysts is also getting increasing attention (Song et al., 2013, Science 6:994-1007; Wang and Rinaldi, 2012, ChemSusChem 5:455-1466). Ni-catalyzed cleavage of aryl ethers in the aqueous phase under mild reaction conditions was recently described (He et al., 2012, J. Am. Chem. Soc. 134:20768-20775). Furthermore, cleavage and hydrodeoxygenation of linkages relevant to lignin conversion with Pd/Zn synergistic catalysis was studied by Abu-Omar and coworkers (Parsell et al., 2013, Chem. Sci. 4:806).

Ford and coworkers have described quantitative depolymerization of organosols lignin (Barta et al., 2010, Green Chemistry 12:1640-1647; U.S. patent application Ser. No. 12/885,397) as well as cellulose and raw lignocelluloses (Matson et al., 2011, J. Am. Chem. Soc. 133:14090-14097; U.S. patent application Ser. No. 12/885,397) over a hydrotalcite derived copper-doped porous metal oxide catalyst ($Cu_{20}PMO$). That process takes place in supercritical methanol and the hydrogen equivalents needed for depolymerization and further reductions originate from the solvent itself upon its reforming. Those studies targeted liquid fuels as products therefore extensive reduction/deoxygenation was desired. Indeed, the aromatic intermediates formed via hydrogenolysis when organosols lignin was used as substrate rapidly underwent further reduction to cyclohexanol derivatives (Barta et al., 2010, Green Chemistry 12:1640-1647).

Interest in corn stover as a feedstock has led to extensive research and investment into the conversion of cellulose and hemicellulose to ethanol by U.S agencies such as DOE, EPA, and DOD, and national FFDRCs such as the National Renewable Energy Laboratory (NREL), as well as by private companies such as Dupont, DSM, Archer Daniels Midland, and Mascoma. As a result, corn stover fermentation plants are being built, and these plants will be generating large amounts of corn lignin as byproduct. Lignin is the second largest component of corn stover after carbohydrates and represents about 18% of the overall mass. Currently, the corn lignin is viewed as a low-value byproduct that is burned on-site for its fuel value. Finding a higher-value chemical use for this material would dramatically improve the economics of the corn stover biorefinery and would further provide a new source of aromatic building blocks, such as phloretic acid, for the chemical industry.

Phloretic acid methyl ester has also been modified through reduction to make diols, such as 4-hydroxybenzenepropanol (Tetrahedron Letters 48 (2007) 8540-8543; U.S. Pat. No. 7,314,889). 4-hydroxybenzenepropanol has found use in polymers (Chemical & Pharmaceutical Bulletin (2001), 49(9), 1234-1235; Polymer (2011), 52(10), 2157-2162.), pharmaceuticals (PCT Int. Appl. (1999), WO 9962878 A1 19991209), and other applications such as photoactive agents (Polymers for Advanced Technologies (2013), 24(5), 473-477; Macromolecules (2001), 34(13), 4291-4293).

Phloretic acid is a naturally occurring molecule that has been extensively studied and has long been viewed as a potentially valuable molecule for a variety of applications. The synthesis of phloretic acid has been presented from variety of chemical precursors. In one example, phenol was alkylated with acrylonitrile in the presence of $AlCl_3$ at 80-120° C. (Chinese Patent Application No. 1200367). Phloretic acid may be synthesized as one example of w-arylalkanoic acids through a Willgerodt-Kindler reaction employing a catalyst comprising HOAc, $Ac_2O$, $H_2SO_4$, $H_2S$, $AcNMe_2$, DMF, or $Na_2SO_4$ (U.S. Pat. No. 5,149,866). De-tert-butylation of 3-(3,5-ditertiary butyl-4-hydroxyphenyl) propionic acid may also yield phloretic acid (Japanese Patent Application No. 63227542). Other examples include alkylation of phenol with acrylonitrile (U.S. Pat. No. 2,789,995) or electrochemical synthesis in the presence of $CO_2$ (French Patent Publication No. 2609474). Apart from the chemical synthesis, phloretic acid has been reported as a compound of a naturally obtained mixture, olive pulp biomass with high phenolic antioxidant content described (European Patent Application No. 1844666).

Phloretic acid has been reported for use in variety of applications, particularly as a precursor for pharmaceuticals or cosmetics, such as in the preparation of antitumor agent 3(4,6)-hydroxy-2-acylphenylacetate (Chinese Patent Publication No. 101407459) or in the synthesis of immunosuppressant and antiproliferative agents (PCT Patent Publication No. 2001072733). Additionally, antihypertensives and ACE inhibitors containing phenylcarboxylic acids, 5-phenyl-γ-valerolactones, or 5-phenyl-4-hydroxyvaleric acids can be synthesized from phloretic acid (Japanese Patent No. 2012144532). p-hydroxycinnamic acid derivatives have also been used in cosmetic or dermatological compositions are discussed (U.K. Patent No. 2431876). Phloretic acid can also be a component of a deodorant (German Patent Application No. 102007028508) and of a skin care cream (Chinese Patent Publication No. 1785158).

Applications of phloretic acid have also been reported in the field of polymers and lubricants, such as the possibility of polymerizing derivatives of phloretic acid (U.K. Patent Application No. 1225290). Feijen and coworkers described injectable chitosan-based hydrogels with phloretic acid as a main ingredient that could serve as artificial extracellular matrix for cartilage tissue engineering (Feijen et al., 2004, Polymer, 45:4653-4662). Other applications include a biodegradable aliphatic/aromatic copolyester polymer from phloretic acid (Korean Patent Publication No. 20060094419), liquid-crystalline hyperbranched and potentially biodegradable polyesters based on phloretic acid and gallic acid (Kricheldorf et al., 1999, Macromolecular Chemical Physics, 200:1784-1791), and uses of lubricating oil antioxidants and stabilizers in the form of (ω-4-hydroxyphenyl)carboxylates (PCT Patent Publication No. 2004050671).

Phloretic acid has been identified as a component of different systems. Examples include phloretic acid as a component of a solder-resistant epoxy resin (Japanese Patent Publication No. 2011046866), a plant growth promoter (Japanese Patent No. 2011162454), and low caloric fat replacers (EP2332427). Phloretic acid has also been described in the preparation of such materials as a compound reducing bitterness of flavan-3-ol (WO2010026003), cyhalothrin derivatives (CN102417468) and optically active IR-absorbing polyurethane (CN101967220).

Phloretic acid has also been identified as a component of several natural compounds. Bartsch and coworkers isolated and purified major phenolic antioxidants, including phloretic acid, from two types of brined olives (Bartsch, et al., 2003, Food and Chemical Toxicology 41:703-717). Ralph and Lu identified the presence of p-coumaroylated units in lignins (Ralph and Lu, 1999, Journal of Agricultural and Food Chemistry, 47:1988-1992), while Yamagata and Sakata determined that phloretic acid is a component of raw dent corn (Sakata and Yamagata, 1980, Journal of the Agricultural Chemical Society of Japan, 54:959-964).

There is a need in the art for energy-efficient methods of depolymerizing lignin from corn stover in order to produce simple mixtures of aromatic products, such as phloretic acid and its derivatives. The present invention addresses this unmet need.

SUMMARY OF THE INVENTION

The present invention relates to a method for producing a monomer from a biopolymer source. The method includes the step of depolymerizing at least one biopolymer from the biopolymer source into a monomer within a system comprised of at least one solvent and at least one catalyst. In one embodiment, the method further includes the step of extracting the at least one biopolymer from the biopolymer source. In another embodiment, the method further includes the step of fractionating the at least one biopolymer from the biopolymer source. In another embodiment, the at least one biopolymer is lignin. In another embodiment, the biopolymer source comprises biomass. In another embodiment, the biomass comprises a nutshell from the candlenut tree. In another embodiment, the at least one solvent is methanol. In another embodiment, the at least one catalyst is a porous metal oxide (PMO) catalyst. In another embodiment, the PMO is comprised of at least one divalent metal cation and at least one trivalent metal cation. In another embodiment, at least one divalent metal cation is selected from the group consisting of copper(II), magnesium(II), manganese(II), and zinc(II). In another embodiment, the at least one trivalent metal cation is selected from the group consisting of aluminum(III), chromium(III), and lanthanum(III). In another embodiment, the catalyst is comprised of two divalent metal cations and one trivalent metal cation. In another embodiment, the two divalent cations are copper(II) and magnesium (II), and the trivalent metal cation is aluminum(III). In another embodiment, the molar ratio of copper(II) to magnesium(II) to aluminum(III) is about 0.03:0.12:0.05. In another embodiment, the molar ratio of total divalent metal cations to total trivalent metal cations is about 3:1. In another embodiment, the system is heated to a temperature no greater than about 120° C. In another embodiment, the system is heated to a temperature no greater than about 180° C. In another embodiment, the system is heated to a temperature no greater than about 220° C. In another embodiment, the system is pressurized to a pressure of about 40 bar. In another embodiment, the system is pressurized by the addition of a gas to the system. In another embodiment, the gas is hydrogen gas. In another embodiment, the steps of extracting the at least one biopolymer from the biopolymer source and depolymerizing at least one biopolymer from the biopolymer source into a monomer both occur within the same system. In another embodiment, the method further includes the step of isolating the monomer from the system. In another embodiment, the method further includes the step of purifying the monomer using a method of purification. In another embodiment, method of purification is column chromatography.

The present invention also relates to a method for producing an oligomer from a biopolymer source. The method includes the step of depolymerizing at least one biopolymer from the biopolymer source into an oligomer within a system comprised of at least one solvent and at least one catalyst. In one embodiment, the method further includes the step of extracting the at least one biopolymer from the biopolymer source. In another embodiment, the method further includes the step of fractionating the at least one biopolymer from the biopolymer source. In another embodiment, the at least one biopolymer is lignin. In another embodiment, the biopolymer source comprises biomass. In another embodiment, the biomass comprises a nutshell from the candlenut tree. In another embodiment, the at least one solvent is methanol. In another embodiment, the at least one catalyst is a porous metal oxide (PMO) catalyst. In another embodiment, the PMO is comprised of at least one divalent metal cation and at least one trivalent metal cation. In another embodiment, at least one divalent metal cation is selected from the group consisting of copper(II), magnesium (II), manganese(II), and zinc(II). In another embodiment, the at least one trivalent metal cation is selected from the group consisting of aluminum(III), chromium(III), and lanthanum (III). In another embodiment, the catalyst is comprised of two divalent metal cations and one trivalent metal cation. In another embodiment, the two divalent cations are copper(II) and magnesium(II), and the trivalent metal cation is aluminum(III). In another embodiment, the molar ratio of copper (II) to magnesium(II) to aluminum(III) is about 0.03:0.12: 0.05. In another embodiment, the molar ratio of total divalent metal cations to total trivalent metal cations is about 3:1. In another embodiment, the system is heated to a temperature no greater than about 120° C. In another embodiment, the system is heated to a temperature no greater than about 180° C. In another embodiment, the system is heated to a temperature no greater than about 220° C. In another embodiment, the system is pressurized to a pressure of about 40 bar. In another embodiment, the system is pressurized by the addition of a gas to the system. In another embodiment, the gas is hydrogen gas. In another embodiment, the steps of extracting the at least one biopolymer from the biopolymer source and depolymerizing the at least one biopolymer from the biopolymer source into a monomer both occur within the same system. In another embodiment, the method further includes the step of isolating the oligomer from the system. In another embodiment, the method further includes the step of purifying the oligomer using a method of purification. In another embodiment, the method of purification is column chromatography.

The present invention also relates to a method for producing a monomer from corn biomass. The method includes the step of depolymerizing corn lignin from the corn biomass into a phloretic acid derivative within a system comprised of at least one solvent and at least one catalyst. In one embodiment, the method further includes the step of extracting the corn lignin from the corn biomass. In another embodiment, the method further includes the step of fractionating the corn lignin from the corn biomass. In another embodiment, the phloretic acid derivative is at least one selected from the group consisting of phloretic acid methyl ester (PAME), phloretic acid ethyl ester, a phloretic acid salt, and any combinations thereof. In another embodiment, the phloretic acid derivative is at least one selected from the group consisting of p-coumaric acid, p-coumaric acid methyl ester, p-coumaric acid ethyl ester, a p-coumaric acid salt, 4-ethylphenol, 4-ethylguaiacol, and any combinations thereof. In another embodiment, the corn biomass is at least one selected from the group consisting of corn grain, corn cobs, corn husks, corn stover, and any combinations thereof. In another embodiment, the at least one solvent is methanol. In another embodiment, the at least one catalyst is a hydrogenation catalyst. In another embodiment, the hydrogenation catalyst is selected from the group consisting of copper, copper chromite, copper (II) carbonate, copper (II) hydrate, copper (II) oxide, copper-zinc oxide, magnesium, magnesium oxide, nickel, palladium, palladium/zinc, Raney nickel, zinc, zinc oxide, a porous metal oxide (PMO) catalyst, and any combinations thereof. In another embodiment, the hydrogenation catalyst is supported on a catalyst support. In another embodiment, the catalyst support is selected from the group consisting of alumina, basic aluminum oxide, barium sulfate, carbon, calcium carbonate, silica, titania, zirconia, and any combinations thereof. In another embodiment, the at least one catalyst has a catalyst loading from about 0.05 weight percent to about 60 weight percent. In another embodiment, the catalyst loading is about 50 weight percent. In another embodiment, the at least one catalyst has a catalyst loading from about 0.5 weight percent to about 25 weight percent. In another embodiment, the system is heated to a temperature from about 120° C. to about 200° C. In another embodiment, the system is heated to a temperature no greater than about 140° C. In another embodiment, the system is heated to a temperature no greater than about 160° C. In another embodiment, the system is pressurized by the addition of a gas to the system. In another embodiment, the gas is hydrogen gas. In another embodiment, the system is pressurized to a pressure from about 10 bar to about 400 bar. In another embodiment, the system is pressurized to a pressure of about 1000 psi. In another embodiment, the steps of extracting the corn lignin from the corn biomass and depolymerizing the corn lignin from the biomass into a phloretic acid derivative both occur within the same system. In another embodiment, the method further includes the step of isolating the phloretic acid derivative from the system. In another embodiment, the method further includes the step of purifying the phloretic acid derivative.

The present invention also relates to a method for producing a monomer from corn biomass. The method includes the step of depolymerizing corn lignin from the corn biomass into a monomer within a system comprised of at least one solvent and at least one hydrogenation catalyst. In one embodiment, the method further includes the step of extracting the corn lignin from the corn biomass. In another embodiment, the method further includes the step of fractionating the corn lignin from the corn biomass. In another embodiment, the monomer is a phloretic acid derivative. In another embodiment, the phloretic acid derivative is at least one selected from the group consisting of phloretic acid methyl ester (PAME), phloretic acid ethyl ester, a phloretic acid salt, and any combinations thereof. In another embodiment, the phloretic acid derivative is at least one selected from the group consisting of p-coumaric acid, p-coumaric acid methyl ester, p-coumaric acid ethyl ester, a p-coumaric acid salt, 4-ethylphenol, 4-ethylguaiacol, and any combinations thereof. In another embodiment, the corn biomass is at least one selected from the group consisting of corn grain, corn cobs, corn husks, corn stover, and any combinations thereof. In another embodiment, the at least one solvent is methanol. In another embodiment, the at least one hydrogenation catalyst is selected from the group consisting of copper, copper chromite, copper (II) carbonate, copper (II) hydrate, copper (II) oxide, copper-zinc oxide, magnesium, magnesium oxide, nickel, palladium, palladium/zinc, Raney nickel, zinc, zinc oxide, a porous metal oxide (PMO) catalyst, and any combinations thereof. In another embodiment, the hydrogenation catalyst is supported on a catalyst support. In another embodiment, the catalyst support is selected from the group consisting of alumina, basic aluminum oxide, barium sulfate, carbon, calcium carbonate, silica, titania, zirconia, and any combinations thereof. In another embodiment, the at least one hydrogenation catalyst has a catalyst loading from about 0.05 weight percent to about 60 weight percent. In another embodiment, the catalyst loading is about 50 weight percent. In another embodiment, the at least one catalyst has a catalyst loading from about 0.5 weight percent to about 25 weight percent. In another embodiment, the system is heated to a temperature from about 120° C. to about 200° C. In another embodiment, the system is heated to a temperature no greater than about 140° C. In another embodiment, the system is heated to a temperature no greater than about 160° C. In another embodiment, the system is pressurized by the addition of a gas to the system. In another embodiment, the gas is hydrogen gas. In another embodiment, the system is pressurized to a pressure from about 10 bar to about 400 bar. In another embodiment, the system is pressurized to a pressure of about 1000 psi. In another embodiment, the steps of extracting the corn lignin from the corn biomass and depolymerizing the corn lignin from the corn biomass into a monomer both occur within the same system. In another embodiment, the method further includes the step of isolating the monomer from the system. In another embodiment, the method further includes the step of purifying the monomer.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 12A is a GPC trace of crude product using 0.5 g $Cu_{20}PMO$ and 1 g lignin at 180° C. (products of Table 6, Entry 3). FIG. 12B is a GPC trace of crude product using 1 g $Cu_{20}PMO$ and 4 g lignin at 180° C. (products of Table 6, Entry 6).

DETAILED DESCRIPTION

Figure 1:
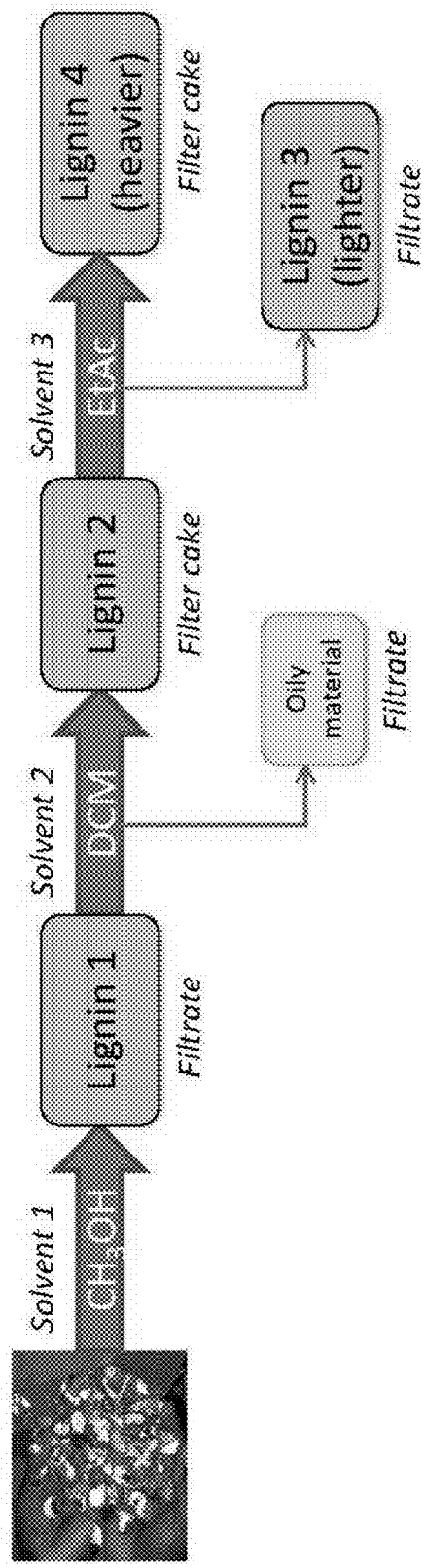
FIG. 1 is a schematic depicting an exemplary extraction and fractionation procedure for obtaining lighter and heavier organosols lignin fractions from Candlenut shells
Figure 2:
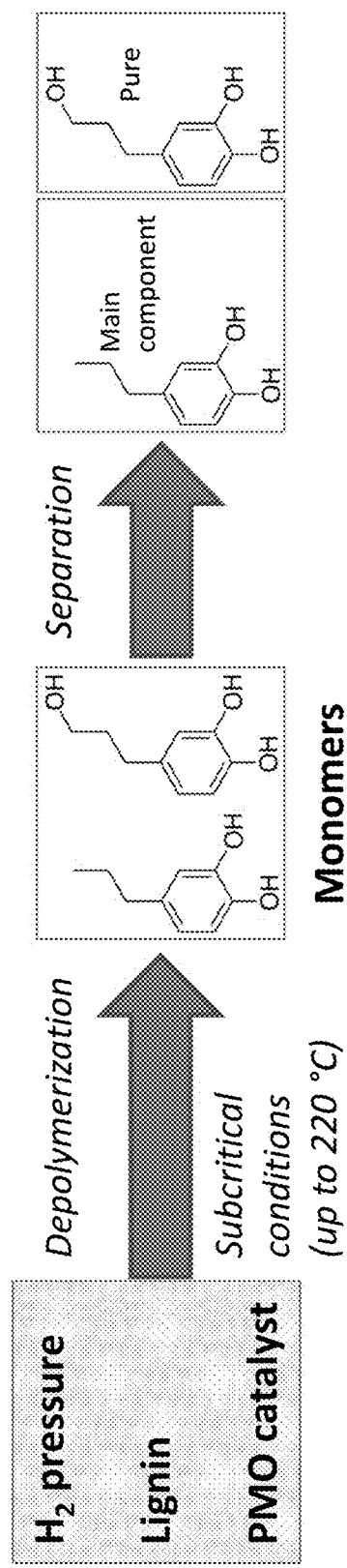
FIG. 2 is a schematic depicting an exemplary isolation procedure of main components by column chromatography.

The present invention relates to the discovery of a novel method for converting lignin into monomers or mixtures of monomers through a depolymerization process. Alternatively, the method can convert lignin into oligomers and/or mixtures of monomers.

The present invention also relates to the discovery of a novel method for converting corn lignin into phloretic acid derivatives through a depolymerization process.

Thus, the present invention provides systems and methods for the production and isolation of monomers from a biopolymer. In one embodiment, the method comprises depolymerizing a biopolymer from a biopolymer source into a monomer. In one embodiment, the method further comprises extracting the biopolymer from the biopolymer source. In another embodiment, the method further comprises fractionating the biopolymer from the biopolymer source. In some embodiments, the biopolymer is lignin. This system is comprised of at least one solvent and at least one catalyst. In some embodiments, the solvent is methanol. Alternatively, the solvent is supercritical methanol. In some embodiments, the at least one catalyst is a porous metal oxide.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The term "aromatic," as used herein, refers to a carbocycle or heterocycle with one or more polyunsaturated rings and having aromatic character, i.e. having (4n+2) delocalized π (pi) electrons, where n is an integer.

The term "supercritical fluid," as used herein, refers to any composition that is above a temperature and pressure at which the phase boundary (e.g., between liquid, gas, or solid) do not exist, i.e., critical state.

The term "phloretic acid," as used herein, refers to 3-(4-hydroxyphenyl)propanoic acid.

The term "p-coumaric acid," as used herein, refers to (E)-3-(4-hydroxyphenyl)-2-propenoic acid.

As used herein the term "salt" includes base addition, acid addition and quaternary salts. Monomers and/or oligomers of the invention which are acidic can form salts with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Monomers and/or oligomers of the invention which are basic can form salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. For a review on suitable salts, see Handbook of Pharmaceutical Salts: Properties. Selection, and Use by Stahl and Wermuth (Wiley-VCH, Weinheim, Germany, 2002).

The terms "fractionate," "fractionating," "fractioned" or "fractionation," as used herein, mean the selective removal of an organic polymer from the system over other organic polymers present within the same system. In some instances, the selective removal of the organic polymer may be due to the difference in solubility of the organic polymer as compared to the other organic polymers or to the affinity and/or reactivity of the organic polymer toward the catalyst as compared to the other lipids. Thus, the term "fractionating" or its related forms can mean removing the organic polymer from the system to form a mixture comprising isolated organic polymer, or it can be used to mean physically isolating and separating the desired organic polymer from the system.

The term "ambient conditions," as used herein, refers to surrounding conditions at about one atmosphere of pressure, 50% relative humidity and about 25° C.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the discovery of a novel method for converting lignin into monomers or mixtures of monomers through a depolymerization process. Alternatively, the method can convert lignin into oligomers and/or mixtures of monomers.

The present invention also relates to the discovery of a novel method for converting corn lignin into phloretic acid derivatives through a depolymerization process.

Thus, the present invention provides systems and methods for the production and isolation of monomers from a biopolymer. In one embodiment, the method comprises depolymerizing a biopolymer from a biopolymer source into a monomer. In one embodiment, the method further comprises extracting the biopolymer from the biopolymer source. In another embodiment, the method further comprises fractionating the biopolymer from the biopolymer source. In some embodiments, the biopolymer is lignin. This system is comprised of at least one solvent and at least one catalyst. In some embodiments, the solvent is methanol. Alternatively, the solvent is supercritical methanol. In some embodiments, the at least one catalyst is a porous metal oxide.

Biomass contains a wide variety of biopolymers, such as lignins, which are useful as fuels and other chemical products. The biopolymer can be extracted from the biomass and subsequently converted into monomers or mixtures or monomers through a depolymerization reaction. Transformation of raw materials, such as lignocellulosic feedstocks, into useful products is challenging due to the complexity of starting materials and the product mixtures generated, and requires specially tailored reaction conditions and catalysts capable of selective bond cleavage reactions. In one embodiment, the present invention provides methods for the depolymerization of lignin, a major component of biomass, to provide well-defined mixtures of aromatic products. Aromatics are an important target compound group since they provide valuable structural features for a variety of industrial applications, especially coatings. The present invention provides advantages over known methods of depolymerization, such as pyrolysis, liquefaction, and hydrolysis techniques, because the methods known in the art mainly result in complex mixtures of products rather than well-defined monomers or oligomers, such as those produced using the present invention. Thus, the present invention provides systems and methods related to the depolymerization of biopolymers isolated from biomass.

In one aspect, the present invention provides methods and systems for the isolation of phloretic acid and/or its methyl or ethyl ester from corn lignin through a depolymerization reaction. While many lignin depolymerization products are currently known, this is the first account of isolating phloretic acid and its derivatives as major products from any lignin treatment process, including reductive depolymerization. In one embodiment, a catalyst of the present invention selectively cleaves the key C—O and C—C linkages found in lignin under reductive conditions, allowing for the *facile* isolation of specific phenylpropanoid subunits. In addition to being highly selective, the conditions are moisture tolerant, and produce very little char, which will greatly extend the life of the catalyst. Therefore, the catalysts of the present invention are useful for lignin depolymerization.

Biopolymer Sources

The present invention relates to the depolymerization of biopolymers from biomass. In one aspect, the present invention relates to the extraction of biopolymers from biomass. A biopolymer source of the present invention comprises at least one biopolymer. Any biopolymer that can undergo a depolymerization reaction is contemplated for use within the systems and methods of the present invention, as would be understood by one skilled in the art. Non limiting examples of biopolymers include lignocelluloses and isolated lignins. In certain embodiments, the biopolymer is lignin. In one embodiment, the lignin is corn lignin.

In certain embodiments, the biopolymer source is biomass. As used herein, the term "biomass" refers to any carbon-containing source of energy or chemicals that is renewable on human timescales. The biomass may be from any source. Biomass may be derived from a single source, or biomass can comprise a mixture derived from more than one source; for example, biomass could comprise a mixture of grass and leaves. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, algae and other marine plants, non-animal oils, palm trees, palm waste biomass such as empty fruit bunches, rapeseed oil, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits and fruit pulps, flowers, and animal manure or a combination thereof. In a preferred embodiment, the biomass is any source of biomass which may yield polymers, oligomers, and/or monomers at least partially comprised of an aromatic molecular structure. In certain embodiments, the biomass is a nutshell. In one embodiment, the nutshell is a candlenut tree nutshell.

In one aspect of the present invention, the biopolymer source is corn biomass. Non-limiting examples of corn biomass include corn grain, corn cobs, corn husks, corn stover, and any combination thereof. In one embodiment, the corn biomass is corn stover.

In some embodiments, the biomass is dried or dewatered prior to being processed by the systems and methods of the present invention. The term "dewatered" as used herein refers to the removal of at least some water. Methods of drying or dewatering biomass are known in the art. Non-limiting methods of drying biomass include ambient air drying, forced air drying, kiln drying, torrefaction, and lyophilization. Non-limiting methods of dewatering biomass include filtration, centrifugation, heating, sedimentation or flotation. In other embodiments, the biomass is wet when processed by the systems and methods of the present invention. In some embodiments, the biomass is processed prior to being subjected to the depolymerization process. In other embodiments, the biomass is not processed prior to the depolymerization process.

Extraction and Fractionation of Biopolymer

In one aspect, the present invention provides systems and methods for the extraction of a biopolymer from a biopolymer source. Any method for extraction known in the art is contemplated for use within the present invention, as would be understood by one skilled in the art. In a preferred embodiment, the biomass is ground to fine particles and stirred in an appropriate amount of solvent for a period of time, after which time the solvent containing the dissolved biopolymer is separated from insoluble material, the solvent is removed, and the biopolymer is isolated. The biopolymer may be isolated using any technique known in the art. Non-limiting examples include organic extraction, drying, heating, separation techniques such as Kraft, soda pulping, mechanical pulping, and steam explosion, and enzymatic or carbohydrate digestion methods such as fermentation and acid hydrolysis. In one embodiment, at least one solvent is used to extract the biopolymer from the biopolymer source. In another embodiment, at least two solvents are used to extract the biopolymer from the biopolymer source. In certain embodiments, the solvent is heated during the extraction procedure. In a preferred embodiment, the solvent is heated to reflux.

In certain embodiments, the systems and methods of the present invention comprise a fractionation step. The properties of a first biopolymer may be different as compared to the properties of a second biopolymer and/or other coproducts found in the biomass, permitting the separation of the first biopolymer from the second biopolymer and/or other coproducts. With fractionation, desired biopolymers can be selectively isolated from other biopolymers and/or coproducts based on properties of the desired biopolymers including, but not limited to, average molecular weight, polarity, chain length, or chemical functionality. In some embodiments, at least one solvent is used for fractionation. In another embodiment, at least two solvents are used for fractionation. In one embodiment, at least one solvent is used to fractionate a biopolymer source into a first and second component, wherein the first component is comprised of biopolymers with an average molecular weight which is lower than the average molecular weight of the second component. In certain embodiments, the solvent is heated during the fractionation procedure. In a preferred embodiment, the solvent is heated to reflux.

As would be understood by one skilled in the art, any solvent in which the biopolymer is soluble is contemplated by the invention. In some embodiments, the solvent is an organic solvent. Non-limiting examples of organic solvents include methanol, ethanol, isopropanol, acetone, dichloromethane, N,N-dimethylformamide, ethyl acetate, acetonitrile, hexane, hexene, octane, pentane, heptane, cyclohexane, iso-octane, and tetrahydrofuran. In one embodiment, the solvent is methanol. In another embodiment, the solvent is dichloromethane. In another embodiment, the solvent is ethyl acetate. In other embodiments, the solvent is water. In some embodiments, the solvent is comprised of a first solvent and a second solvent. In one embodiment, the first solvent is water and the second solvent is an organic solvent. In some embodiments, acid is added to the solvent. In other embodiments, base is added to the solvent. In one embodiment, the solvent is aqueous acid. In another embodiment, the solvent is aqueous base. Alternatively, in certain embodiments the solvent is a supercritical fluid. Non-limiting examples of supercritical fluids include supercritical carbon dioxide ($scCO_2$) and supercritical methanol (scMeOH).

In some embodiments, two or more extraction and/or fractionation sequences are performed sequentially. In one embodiment, a first extraction is followed by a first fractionation and a second fractionation. The use of sequential extractions and/or fractionations permits the separation of biopolymers with different properties, such as average molecular weights, different chain lengths, polarity, or chemical functionality, based on the solubility of each biopolymer in the solvent(s).

Depolymerization

The present invention provides systems and methods for the depolymerization of a biopolymer into a monomer. The present invention also provides systems and methods for the depolymerization of a biopolymer into a mixture of monomers. The present invention also provides systems and methods for the depolymerization of a biopolymer into an oligomer. In one embodiment, the depolymerization reaction is performed under subcritical conditions. In another embodiment, the depolymerization reaction is performed under supercritical conditions.

Any monomer and/or oligomer that can be produced by depolymerizing a biopolymer is contemplated by the present invention, as would be understood by one skilled in the art. In a preferred embodiment, the monomer is an aromatic monomer. In one embodiment, the monomer is a phenylpropanoid. In one embodiment, the monomer is selected from the group consisting of 4-propylcatechol, 4-(3-hydroxypropyl)catechol, 2,3-dihydro-1H-indene-5,6-diol, 4-(3-methoxypropyl)catechol, and any combinations thereof. In one embodiment, the monomer is phloretic acid.

In one aspect of the invention, the monomer is a phloretic acid derivative. Examples of phloretic acid derivatives include, but are not limited to, phloretic acid methyl ester (PAME), phloretic acid ethyl ester, phloretic acid salts, as well as unsaturated versions of phloretic acid such as p-coumaryl derivatives, as well as derivatives with additional hydroxyl or alkoxyl substitution on the aromatic ring. Non-limiting examples of p-coumaryl derivatives include p-coumaric acid, p-coumaric acid methyl ester, and p-coumaric acid ethyl ester. In one embodiment, the phloretic acid derivative is at least one selected from the group consisting of phloretic acid methyl ester (PAME), phloretic acid ethyl ester, a phloretic acid salt, and any combinations thereof. In one embodiment, the phloretic acid derivative is phloretic acid methyl ester (PAME). In another embodiment, the phloretic acid derivative is phloretic acid ethyl ester. In one embodiment, the phloretic acid derivative is at least one selected from the group consisting of p-coumaric acid, p-coumaric acid methyl ester, p-coumaric acid ethyl ester, a p-coumaric acid salt, and any combinations thereof. In one embodiment, the monomer is 4-ethylphenol, 4-ethylguaiacol, or a combination thereof.

In certain embodiments of the present invention, the system is comprised of at least one solvent. In other embodiments, the system is comprised of at least two solvents. As would be understood by one skilled in the art, any solvent in which the biopolymer is soluble is contemplated by the invention. In one embodiment, the solvent is water. In some embodiments, the solvent is an organic solvent. Non-limiting examples of organic solvents include methanol, ethanol, isopropanol, acetone, dichloromethane, N,N-dimethylformamide, ethyl acetate, acetonitrile, hexane, hexene, octane, pentane, heptane, cyclohexane, iso-octane, and tetrahydrofuran. In a preferred embodiment, the solvent is methanol. In one embodiment, the solvent is a mixture of water and at least one organic solvent. Alternatively, in certain embodiments the solvent is a supercritical fluid. Non-limiting examples of supercritical fluids include supercritical carbon dioxide ($scCO_2$) and supercritical methanol (scMeOH). In a preferred embodiment, the solvent is scMeOH.

The systems and methods of the present invention may further include at least one catalyst for depolymerization. In one embodiment, the catalyst is homogenous. In another embodiment, the catalyst is heterogenous. Examples of heterogenous catalysts include, but are not limited to, Co, Cu, Mg, Mo, Ni, Pd, Pt, Rh, Ru, Zn, or combinations of these metals supported on aluminum oxide, basic aluminum oxide, activated carbon, carbon black, carbon nanotubes, cerium oxide, copper (II) carbonates, copper (II) hydrates, magnesium oxide, polyoxometallates, silica, silicon oxides, zeolites, zinc oxide, or zirconium oxide; ionic liquids on solid supports, metal or metal oxide nanoparticles, metal nitrides, and metal oxides. In one embodiment, the catalyst is a metal oxide. In another embodiment, the catalyst is a supported metal oxide, for example, copper (II) oxide on alumina. In yet another embodiment, the catalyst is a basic metal carbonate or supported basic metal carbonate, for example, $Cu_3(OH)CO_3$/alumina. In one embodiment, the catalyst is a porous metal oxide (PMO). PMOs can be prepared by the calcination of hydrotalcite-like (HTC) precursors, as would be understood by one skilled in the art. See, for example, Cavani et al., 1991, Catalysis Today 11:173-301, which is hereby incorporated by reference in its entirety. In some embodiments, the catalyst is an acid catalyst. In other embodiments, the catalyst is a basic catalyst. In other embodiments, the catalyst is a neutral catalyst.

The PMOs of the present invention contain at least one divalent metal cation and at least one trivalent metal cation. In one embodiment, the molar ratio of total divalent metal cations to total trivalent metal cations ranges from about 100:1 to 1:100. In another embodiment, the molar ratio of total divalent metal cations to total trivalent metal cations ranges from about 10:1 to about 1:10. In another embodiment, the molar ratio of total divalent metal cations to total trivalent metal cations ranges from about 5:1 to about 1:5. In a preferred embodiment, the molar ratio of total divalent metal cations to total trivalent metal cations is about 3:1. A metal cation is the cation of a metal selected from the group including: for example, Mg, Al, Cr, Mn, Ti, Zn, Zr, Si, Cu, Ni, Pd, W, Sn, Nb, Au, Co, Ir, Rh, Ru, Pt, Ce, Ba, Bi, Fe, Hf, La, Se, Ta, Sr, Sn, V, W, Nd, Yb, Ag, Ge and Y. In one embodiment, the divalent metal cation is selected from the group consisting of copper(II), magnesium(II), manganese (II), and zinc(II). In a preferred embodiment, the divalent metal cation is copper(II). In one embodiment, the trivalent metal cation is selected from the group consisting of aluminum(III), chromium(III), and lanthanum(III).

In some embodiments, a dopant is used in a PMO to replace a metal cation with a different metal cation of the same valence. In certain embodiments, the PMO is comprised of two or more different divalent metal cations and/or two or more different trivalent metal cations, wherein the molar ratio of total divalent metal cations to total trivalent metal cations is about 3:1. In one embodiment, the molar ratio of one divalent metal cation to one trivalent cation is 0.15:0.05. In another embodiment, the molar ratio of two different divalent metal cations to one trivalent cation is 0.03:0.12:0.05. In another embodiment, the molar ratio of one divalent metal cation to two different trivalent cations is 0.15:0.04:0.01. In another embodiment, the molar ratio of two different divalent metal cations to two different trivalent cation is 0.03:0.12:0.04:0.01. In another embodiment, the molar ratio of three different divalent metal cations to one trivalent cations is 0.03:0.03:0.09:0.05.

In some embodiments, the PMO is comprised of one divalent metal cation and one trivalent metal cation. In one embodiment, the divalent metal cation is magnesium(II) and the trivalent metal cation is aluminum(III). In other embodiments, the PMO is comprised of two divalent metal cations and one trivalent metal cation. In one embodiment, the two divalent metal cations are copper(II) and magnesium(II), and the trivalent metal cation is aluminum(III). In another embodiment, the two divalent metal cations are zinc(II) and magnesium(II), and the trivalent metal cation is aluminum (III). In other embodiments, the PMO is comprised of one divalent metal cation and two trivalent metal cations. In one embodiment, the divalent metal cation is magnesium(II), and the two trivalent metal cations are aluminum(III) and chromium(III). In another embodiment, the divalent metal cation is magnesium(II), and the two trivalent metal cations are aluminum(III) and lanthanum(III). In other embodiments, the PMO is comprised of two divalent metal cations and two trivalent metal cations. In one embodiment, the two divalent metal cations are copper(II) and magnesium(II), and the two trivalent metal cations are aluminum(III) and chromium(III). In one embodiment, the two divalent metal cations are copper(II) and magnesium(II), and the two trivalent metal cations are aluminum(III) and lanthanum (III). In other embodiments, the PMO is comprised of three divalent metal cations and one trivalent metal cation. In one embodiment, the three divalent metal cations are copper(II), manganese(II), magnesium(II), and the trivalent metal cation is aluminum(III).

In one aspect, the catalyst of the present invention is a hydrogenation catalyst. Non-limiting examples of hydrogenation catalysts include metals such as nickel, copper, chromium, cobalt, magnesium, nickel, rhodium, ruthenium, rhenium, osmium, iridium, platinum, palladium, platinum black, zinc; copper chromite, copper (II) carbonate, copper (II) hydrate, copper (II) oxide, copper-zinc oxide, magnesium oxide, zinc oxide, a PMO, compounds thereof and combinations thereof. Raney-type catalysts may be formed from some of the metals listed above (for example, Raney Nickel® (W.R. Grace & Co., Columbia, Md.)), and these Raney-type catalysts are also expected to be useful as hydrogenation catalysts for the present invention. A promoter such as, without limitation, tin, zinc, copper, gold, silver and combinations thereof may be used to affect the reaction, for example, by increasing activity and catalyst lifetime. In one embodiment, the hydrogenation catalyst is selected from the group consisting of copper chromite, copper oxide, copper-zinc oxide, palladium, palladium/zinc, Raney nickel, and a PMO. In another embodiment, the hydrogenation catalyst can be a commercial catalyst, for example, Nysosel catalysts produced by BASF.

In one embodiment, the hydrogenation catalyst of the present invention is supported on a catalyst support. Examples of catalyst supports include, but are not limited to, oxides such as silica, alumina, basic alumina, titanic, and zirconia; barium sulfate; calcium carbonate; carbon, particularly acid washed carbon; and combinations thereof. The catalyst support can be in the form of powder, granules, pellets, or the like. The supported hydrogenation catalyst can be prepared by depositing the hydrogenation catalyst on the support by any number of methods well known to those skilled in the art of catalysis, such as spraying, soaking or physical mixing, followed by drying, calcination, and if necessary, activation through methods such as reduction.

In one embodiment, the catalyst loading of a catalyst of the present invention is from about 0.05 weight percent to about 60 weight percent based on the weight of the biopolymer. In another embodiment, the catalyst loading of a catalyst of the present invention is from about 0.5 weight percent to about 50 weight percent. In another embodiment, the catalyst loading of a catalyst of the present invention is from about 2.5 weight percent to about 30 weight percent. In another embodiment, the catalyst loading of a catalyst of the present invention is from about 0.5 weight percent to about 25 weight percent. In one embodiment, the catalyst loading of a catalyst of the present invention is about 25 weight percent. In another embodiment, the catalyst loading of a catalyst of the present invention is about 50 weight percent. In another embodiment, the catalyst loading of a catalyst of the present invention is about 60 weight percent. In one embodiment, the catalyst is loaded in a fixed bed. In another embodiment, the catalyst is loaded in a slurry wherein the process is operated continuously.

In certain embodiments, the depolymerization of a biopolymer into a monomer may be performed in two steps, where the first step comprises extraction and/or fractionation of a biopolymer from a biopolymer source and the second step comprises the depolymerization of a biopolymer into a monomer. In one embodiment, the extraction and/or fractionation and the depolymerization are performed simultaneously within the same system. The systems and methods of producing a monomer from a biopolymer described herein are comprised of both the step of extracting the biopolymer from the biopolymer source and the step of depolymerizing the biopolymer into the monomer. The systems of the present invention are comprised of a number of variables that can be adjusted in order to effectively depolymerize the biopolymer. These variables include solvents, volume of solvent, temperature, pressure, amount and identity of catalyst, and reaction time.

In some embodiments, the system is heated in a temperature range from 30° C. to 500° C. In one embodiment, the system is heated in a temperature range from 120° C. to 200° C. In one embodiment, the system is heated in a temperature range from 140° C. to 160° C. In a preferred embodiment, the system is heated to a low temperature. In one embodiment, the temperature is no greater than about 220° C. In yet another embodiment, the temperature is no greater than about 180° C. In yet another embodiment, the temperature is no greater than about 160° C. In yet another embodiment, the temperature is no greater than about 140° C. Alternatively, the system is heated to a high temperature. In one embodiment, the temperature is no greater than about 310° C. In one embodiment, the temperature of the system is held constant. In another embodiment, the temperature of the system is increased over time. In another embodiment, the temperature of the system is decreased over time.

In some embodiments, pressure is applied to the system. The pressure can be any pressure that is sufficient to promote the depolymerization of a biopolymer into one or more monomers, as would be understood by a skilled artisan. In some embodiments, a gas is added to the system to increase the pressure. Non-limiting examples of a gas include nitrogen, argon, and hydrogen. In a preferred embodiment, the gas is hydrogen. In one embodiment, the initial pressure of the system at room temperature is between 10 bar and 400 bar. In one embodiment, the initial pressure of the system at room temperature is between 0.1 bar and 100 bar. In another embodiment, the pressure of the system is between 30 bar and 100 bar. In another embodiment, the initial pressure of the system at room temperature is between 1 bar and 75 bar. In yet another embodiment, the initial pressure of the system at room temperature is between 5 bar and 50 bar. In one embodiment, the pressure of the system is about 1000 psi. In one embodiment, the pressure of the system is about 70 bar. In one embodiment, the initial pressure of the system at room temperature is about 40 bar. In another embodiment, the pressure of the system is between 0.1 and 100 bar. In one embodiment, the pressure of the system is held constant. In another embodiment, the pressure of the system is increased over time. In another embodiment, the pressure of the system is decreased over time.

The process of depolymerizing the biopolymer into a monomer is carried out over a period of time known as the reaction time. As used herein, the term "reaction time" refers to an amount of time effective for the depolymerization of at least some biopolymers into monomers, mixtures of monomers, and/or oligomers. In one embodiment, the reaction time is between 0.1 hours to 10 hours. In another embodiment, the reaction time is between 0.5 hours to 20 hours. In another embodiment, the reaction time is between 1 hour to 12 hours. In one embodiment, the reaction time is at least 40 minutes. In another embodiment, the reaction time is at least 60 minutes. In a certain embodiment, the reaction time is at least 2 hours. In another embodiment, the reaction time is at least 3 hours. In another embodiment, the reaction time is at least 4 hours. In another embodiment, the reaction time is at least 6 hours. In another embodiment, the reaction time is at least 8 hours. In another embodiment, the reaction time is at least 10 hours. In another embodiment, the reaction time is at least 12 hours. In another embodiment, the reaction time is at least 14 hours. In another embodiment, the reaction time is at least 18 hours. In another embodiment, the reaction time is at least 20 hours.

The monomers can be isolated from the system using any method known in the art. In one such method, the monomers can be separated from the catalyst by filtration, and can then be separated from solvent by rotary evaporation. If necessary, the monomers can be further purified by any method known in the art, such as column chromatography, crystallization, precipitation, distillation, liquid-liquid extraction, or membrane separations. In a preferred embodiment, the monomers are purified using column chromatography.

In one aspect, the monomers of the present invention can be submitted to subsequent chemical modifications, as understood by one skilled in the art. These modifications include a variety of derivatizing chemical reactions, such as reduction, oxidation, esterification, saponification, and the like. In one embodiment, phloretic acid methyl ester (PAME) is reduced to provide 4-hydroxybenzenepropanol.

Reaction System

The systems and methods of the present invention may be carried out within a reaction vessel. A reaction vessel of any size, shape, or internal volume may be used within the systems and methods of the present invention. In some embodiments, the reaction vessel is a reactor. In one embodiment, the reaction vessel is a continuous stirred tank reactor (CSTR). In another embodiment, the reaction vessel is a continuous reactor, for example, a plug flow reactor (PFR). In yet another embodiment, the reaction vessel is a hydrogenator or other type of pressurized vessel. In certain embodiments, the reaction vessel comprises at least one inlet passage and at least one outlet passage. The at least one inlet passage and the at least one outlet passage permit reaction components to enter and/or exit the reaction vessel. In one embodiment, the reaction vessel has a fixed volume. In certain embodiments, the reaction vessel is suitable for performing the reactions described hereinthroughout. Reaction components may be added to a reaction vessel such that the depolymerization and/or extraction and fractionation reactions may be performed within the reaction vessel. Non-limiting examples of reaction components include a reaction substrate, such as a biopolymer source, a reaction product, such as a monomer, a solvent, and a catalyst. In one embodiment, a biopolymer, a solvent, and at least one catalyst are added to a reaction vessel, and the depolymerization reaction is performed on the reaction components within the reaction vessel.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the systems and methods of the present invention for producing a monomer from a biopolymer source and practice the claimed methods. The following working examples therefore, specifically point out the preferred embodiments of the present invention, and are not to be construed as limiting in any way the remainder of the disclosure.

Example 1: Mild Depolymerization of Candlenut Shell Lignin Over Doped Porous Metal Oxides The results described herein demonstrate the isolation of aromatics via mild depolymerization of lignin and utilized candle nutshells as the biomass source. It was found that organosols lignin could be obtained in particularly high yields using simple extraction procedures from this plant. The obtained crude product was further fractionated to lighter and heavier components. While the heavier fraction could be depolymerized over a variety of porous metal oxides in supercritical methanol to complex mixtures in the desired molecular weight range, the lighter fraction underwent highly selective depolymerization to well defined aromatics using significantly milder reaction conditions. Methods using gel permeation chromatography were developed to concentrate on following molecular weight changes during these transformations. It was observed that catalyst composition had little effect on depolymerization in the supercritical regime in terms of molecular weight distribution, whereas in the subcritical runs, product distribution strongly depended on the chemical composition of the porous metal oxide used.

The materials and methods employed in these experiments are now described.

Materials

Candlenut shells (from *Aleurites moluccana*; Euphorbiaceae) were obtained from Kasese District, Uganda. The nutshells were rinsed in water to remove soil and debris and then air-dried at room temperature. The moisture content of the nutshells was determined to be 9.6% by drying to constant weight at 105° C. The nutshells were ground in a handmill and passed through standard sieves (ASTME-11)

to obtain particles of 250 μm-1 mm in diameter (60-18 mesh). NMR Spectra were recorded at 25° C. in an Avance 500 MHz instrument (Bruker Biospin, Billerica, Mass.). MeOH (99.8%, anhydrous) used as reaction medium were from Acros. MeOH used for washing the catalyst were from Merck. $Mg(NO_3)_2 \cdot 4H_2O$ (>99.0%), $Cu(NO_3)_2 \cdot 2.5H_2O$ (98%), $Cr(NO_3)_3 \cdot 9H_2O$ (99.0%), $Mn(NO_3)_2 \cdot 4H_2O$ (>97.0%) were purchased from Sigma Aldrich, $La(NO_3)_3 \cdot 6H_2O$ (>99.0%) was obtained from Fluka. $Al(NO_3)_3 \cdot 9H_2O$ (98.7%), $Na_2CO_3 \cdot H_2O$ (p.a.) were purchased from J. T. Baker. NaOH (98.6%) was purchased from Mallinckrodt Chemicals. Solvents for extraction procedures were reagent grade. All chemicals were used as received without further purification.

Exemplary Procedure for Candlenut Shells Extraction

In a 2 L round bottom flask, 500 ml methanol and 110 g finely ground candlenut shells were combined. The flask was heated under reflux overnight, and then cooled to room temperature. The dark brown liquid was separated from the shell pieces by filtration in vacuo and washed additionally with small portions of methanol. The combined washings were concentrated by rotary evaporation to 100-200 mL and the recovered methanol was saved. The concentrated brown solution was poured over 2 L of ice in 4-8 aliquots under vigorous stirring until light brown Lignin 1 precipitated. The ice and lignin mixture was filtered and dried under vacuum. The filter cake was additionally washed with small aliquots of ice-cold water and dried. (13.62 g, 12.4% yield)

Exemplary Procedure for Purification of Lignin 1

8.39 grams of Lignin 1 were extracted with 150 ml refluxing DCM in a 1 L round bottom flask overnight. The mixture of darker solid and yellowish liquid was filtered under vacuum and the filter cake was washed with small amount of DCM. The solvent was evaporated and yellowish oil (0.2663 g, 3.1% yield) was obtained. The brown solid (Lignin 2, 8.077 g) was dried and analyzed by gel permeation chromatography.

Exemplary Procedure for Fractionation of Lignin 2

Lignin 2 (7.29 g) was placed in a 2 L round bottom flask equipped with a reflux condenser, and was heated at reflux with 400 ml ethyl acetate overnight, followed by cooling to room temperature. The filter cake was washed with ethyl acetate until the washings were clear. From the combined filtrate the solvent was removed, yielding a light brown solid (Lignin 3, 4.976 g) which was subjected to GPC analysis. The filter cake (Lignin 4, 2.85 g) was dried and subjected to GPC analysis.

Catalyst Preparation

The porous metal oxides were prepared following a previously described procedure using 0.05 mol $Al(NO_3)_3 \cdot 9H_2O$ and 0.15 mol $Mg(NO_3)_2 \cdot 6H_2O$ (Hansen et al., 2012, Green Chem. 14:2457-2461. Variants of the catalyst were synthesized by doping magnesium and aluminum with different proportions of copper, lanthanum, manganese, chromium or zinc respectively.

Exemplary Procedure for Catalyst Preparation

A solution of $Al(NO_3)_3 \cdot 9H_2O$ (18.76 g, 0.05 mol) and $Mg(NO_3)_2 \cdot 6H_2O$ (38.46 g, 0.13 mol) in 300 mL water was added drop wise over a period of 1-2 hours to a solution of $Na_2CO_3$ (6.2 g, 0.05 mol) in 375 mL water preheated to 65° C. under vigorous stirring. Small aliquots of 1M NaOH were added periodically to maintain a pH of 10. The solution was left stirring for 3 days at 65° C. The resulting slurry was collected by vacuum filtration and the solids were washed with water (~1.5 L) until chloride free. Subsequently, the filter cake was re-suspended in 2M warm aqueous $Na_2CO_3$ and left to stir for at least three hours. The resulting mixture was vacuum filtered and washed with at least 500 mL of deionized water. The obtained hydrotalcite was dried in an oven at 100° C. and its structure was verified with powder X-ray measurement. The hydrotalcite was then calcined at 460° C. over 24 hours to yield the corresponding PMO.

Catalytic Disassembly of Lignin 4 in the Supercritical Regime 100 mg PMO, 100 mg Lignin 4, and 3 mL methanol were combined in a 10 mL stainless steel bomb. The vessels were heated to 300° C. for a designated period of time then rapidly cooled in ice water (Tables 5-8). The whole content of the vessel was transferred to centrifuge tubes and additionally washed with small amounts of methanol. The suspensions were centrifuged at 70 rpm over 20 minutes. The liquids were then decanted. The solids remaining in the centrifuge tubes were shaken with 6 mL methanol and centrifuged. This procedure was repeated 2 times. All washings were combined with the decanted solution and the solvent was removed by rotary evaporation. The weight of the liquid phase products was determined and they were analyzed by GPC and NMR. The solids remaining in the centrifuge tube were additionally washed with 5 mL diethyl ether and the washing discarded. The solids were thoroughly dried in a desiccators and the amount of solids was determined. To a fraction of the solids, concentrated $HNO_3$ was added to test for char.

Exemplary Procedure for Parr Reactor Experiments with Added $H_2$

A solution of an indicated amount of Lignin 3 in 30 mL methanol and an indicated amount of $Cu_{20}PMO$, were combined in a 100 mL Parr reactor equipped with magnetic stirrer and controller. The reactor was pressurized with 40 bar $H_2$ at room temperature. The vessel was then heated to 140-220° C. (Table 3) and the desired temperature established within 30-40 minutes. The vessel was stirred for the indicated time period at 700 rpm, than the heating mantle was exchanged to an ice-water bath. After room temperature was established, the pressure was noted and the vessel was slowly depressurized. A colorless solution that turned dark on air and purple-colored solids were obtained. The entire content of the reactor was transferred to centrifuge tubes with additional portions of methanol when needed, and the suspensions were centrifuged. The solutions were decanted, and the solids were additionally washed with 2×10 ml methanol and the washings combined with the decanted liquid. The solvent was removed and dark viscous material was obtained. Samples for NMR and GPC measurements were taken. The solids were additionally washed with 2×5 ml diethyl ether and dried in a desiccator in vacuo. The mass of the solids was determined.

NMR Details of an Exemplary Crude Product Mixture:

$^1H$ NMR ($CD_3OD$, 500 MHz) δ (ppm): 0.85 (3H, t, J=14 Hz) (A-$CH_3$); 1.52 (m, 2H, J=14 Hz) (A-$CH_2$); 1.70-1.75 (m, 2.6H, J=13 Hz) (B—$CH_2$ and D-$CH_2$); 1.94 (m, 1.28H, J=15 Hz) (C—$CH_2$); 2.37 (t, 2H, J=15 Hz) (A-$CH_2$); 2.44-2.49 (m, 2.88H, J=16 Hz) (B—$CH_2$ and D-$CH_2$); 2.68 (t, 2.51H, J=15 Hz) (C—$CH_2$); 3.26 (b, 0.63H) (D-$OCH_3$); 3.31 (m, 1.79H) (D-$CH_2$); 3.50 (t, 1.52H, J=13 Hz) (B—$CH_2$); 6.50 (m, 2.51H, J=15 Hz, 4 Hz); 6.64-6.68 (m, 6.8H).

$^{13}C$ NMR ($CD_3OD$, 500 MHz) δ (ppm): 13.2 (A); 25.0 (A); 25.9 (C); 31.3 (D); 31.5 (B and D); 32.6 (C); 34.8 (B); 37.5 (A); 57.8 (D); 61.5 (B); 72.2 (D); 112.09 (A); 116.13 (A); 116.23 (B); 116.52 (B); 120.62 (B); 120.65; 134.96 (B); 135.50 (A); 136.00; 143.95 (A); 144.12 (B); 144.59 (C); 145.90 (A); 146.02 (B)

(A)=4-propylcatechol
(B)=4-(3-hydroxypropyl)catechol
(C)=2,3-dihydro-1H-indene-5,6-diol (proposed structure)
(D)=4-(3-methoxypropyl)catechol (proposed structure)

Column Chromatography

A crude mixture obtained from a Parr reactor experiment was subjected to column chromatography with eluents chloroform/methanol (20:1). The first 10-14 fractions were carefully collected in 1-2 ml portions, and product was identified in the eluent using thin layer chromatography (TLC). After the first two spots eluted, the eluent was changed to chloroform/methanol 3:1 and the next set of fraction was collected in 10 ml portions. The eluent was changed to methanol in order to flush the column, and the final washings were collected in a round bottom flask. The detailed description of fractions collected in the various column experiments is summarized in Table 1 and FIGS. 15-24.

TABLE 1

Details of the column chromatography experiments

|  | Column 1 (0.350 g) |  | Column 2 (0.534 g) |  | Column 3 (909.2 mg) |  |
|---|---|---|---|---|---|---|
| Products A, C, and D | Fr 1-2 | 6 mg | Fr 1-3 | 95.3 mg | Fr 1-5 | 67.8 |
|  | Fr 3-7 | 30.20 mg | Fr 4-10 | 174.7 mg | Fr 6-7 | 101.5 |
|  | Fr 8-14 | 61.5 mg | Fr 11-13 | 91.4 mg | Fr 8 | 34.2 |
| Product B = 4-(3-hydroxypropyl)-catechol | Fr 14-20 | 177.5 mg | Fr 14-27 | 131.2 mg | Fr 9-18 | 433.1 |
| Decomposition or oligomeric products | Fr-last | 8.8 mg | Fr 28-35 | 93.3 mg | Fr-Last | 180.5 |

NMR Details of the Separated Components:

4-propylcatechol A (main)+C+D:

$^1$H NMR (CD$_3$OD, 500 MHz) δ (ppm): 0.85 (t, 3H, J=14 Hz) (A-CH$_3$); 1.52 (m, 2H, J=15 Hz) (A-CH$_2$); 1.70-1.75 (m, 0.87H, J=14 Hz) (D); 1.94 (m, 0.57H, J=14 Hz) (C); 2.37 (t, 2H, J=15 Hz) (A-CH$_2$); 2.44-2.49 (m, 1H, J=13 Hz) (D-CH$_2$), 2.68 (t, 1H, J=15 Hz) (C—CH$_2$); 3.26 (b, 1.68H) (D-OCH$_3$); 3.31 (b, 1.33H) (D-CH$_2$); 6.439-6.50 (m, 1.3H, J=15 Hz) (Ar); 6.577-6.682 (m, 3.46H, J=16 Hz, J=6 Hz) (Ar)

$^{13}$C NMR (CD$_3$OD, 500 MHz) δ (ppm): 14.06 (A); 25.88 (A); 26.90 (C); 32.36 (D); 33.47 (C); 35.60 (D); 38.39 (A); 58.72; 62.31 (D); 112.13 (C); 116.14 (A); 116.56 (A); 120.70 (A); 134.69 (D); 135.47 (A); 135.97 (C); 144.05 (A); 144.61; 145.92 (A)

4-(3-hydroxyproyl)-1,2-Benzenediol (B)

$^1$H NMR (CD$_3$OD, 500 MHz) δ (ppm): 1.73 (m, 2H, J=13 Hz) (B: CH$_2$); 2.47 (t, 2H, J=16 Hz) (B: CH$_2$—Ar); 3.50 (t, 2H, J=13 Hz) (B: CH$_2$—O); 6.50 (m, 1H) (B$_{Ar}$); 6.64-6.68 (m, 2H) (B$_{Ar}$)

$^{31}$C NMR (CD$_3$OD, 500 MHz) δ (ppm): 32.4 (B: CH$_2$); 35.6 (B: CH$_2$—Ar); 62.3 (B: CH$_2$—O); 116.2 (B); 116.5 (B); 120.6 (B); 135.0 (B); 144.2 (B); 146.0 (B)

MS: ESI-MS, negative mode, (m/z) 151.18 (A), 168.11 (B), 181.11 (D).

The results of the experiments are now described.

Isolation of Suitable Lignin Source

Extraction of the candlenut shells with refluxing methanol gave excellent yields of organosols lignin. Prior to extraction, the shells were washed and dried, followed by mechanical cracking (Klein et al., 2010, J. Agric. Food Chem. 58:18). The extraction procedure was carried out using methods previously described for wood (Harris et al., 1938, J. Am. Chem. Soc. 60:1467-1470), albeit with slight modifications.

Figure 3:
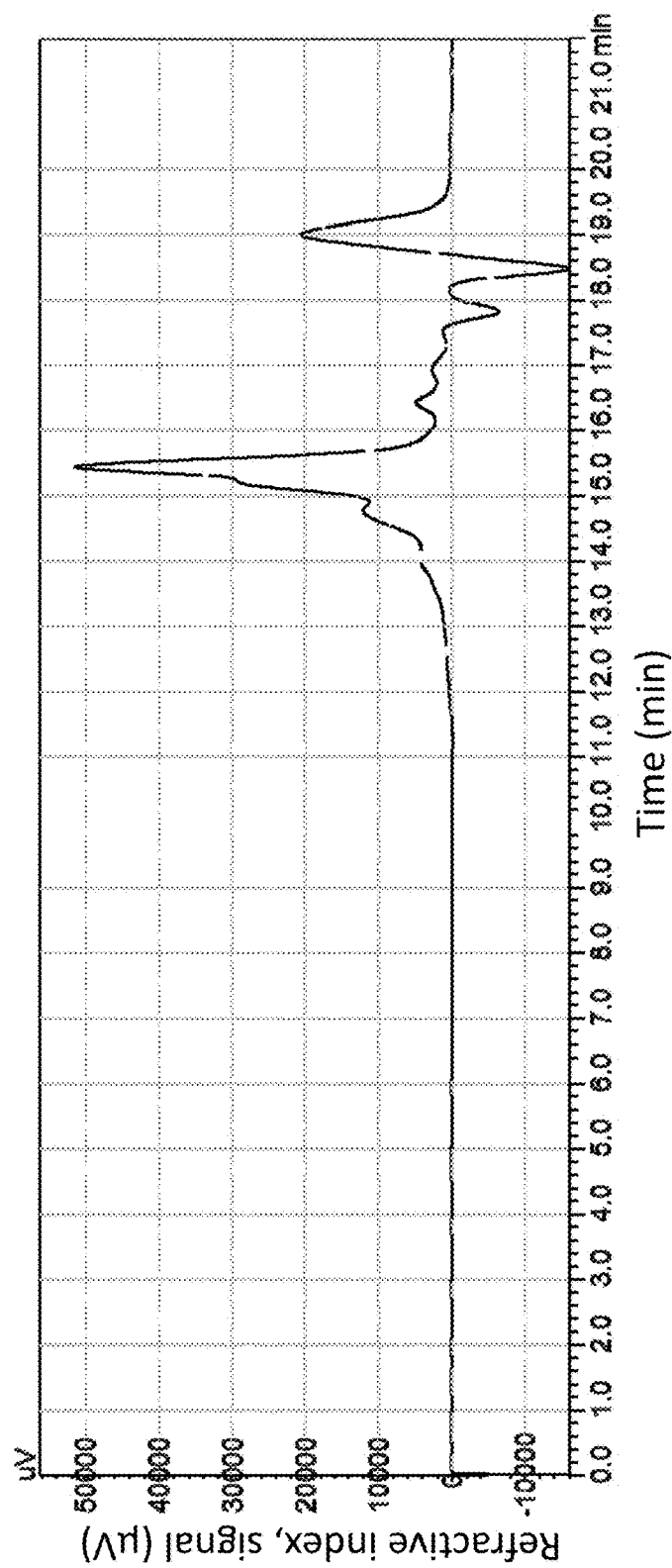
FIG. 3 is a GPC trace depicting the oily material extracted with dichloromethane, $M_n$=242; $M_w$=595.

In these experiments, 80-600 g of finely ground raw material was extracted overnight with an appropriate amount of boiling methanol, and in the absence of acid or base. The crude lignin (Lignin 1) was precipitated over ice, and then filtered. The weight of Lignin 1 was determined to be 7.9-70.6 g, indicating an 11.9% average yield (Table 2). Gel Permeation Chromatography (GPC) measurement identified an average molecular weight of 1162 g/mol with a relatively broad molecular weight range [$M_v/M_n$=1.347]. Therefore, Lignin 1 was further subjected to extraction and fractionation with a variety of common organic solvents. 0.27-0.50 g of yellow oil were extracted with refluxing dichloromethane from 8.4-21.5 g beige crude material, which displayed a sharp GPC signal with $M_w$=595 g/mol and $M_n$=242 g/mol (FIG. 3). $^1$H NMR spectroscopy revealed that the structure of the yellow oil is not lignin-like but rather aliphatic in nature.

TABLE 2

Reproduced Extraction Procedures and Corresponding Yields

| Entry | Nutshells (g) | Lignin 1 (g) | Yield (%) | Entry | Lignin 1 (g) | Oil | Yield (%) |
|---|---|---|---|---|---|---|---|
| 1 | 80 | 7.95 | 9.9 | 1 | 21.5 | 0.5 | 2.3 |
| 2 | 110 | 13.62 | 12.4 | 2 | 17.06 | 0.483 | 2.8 |
| 3 | 170 | 21.58 | 12.7 | 3 | 8.39 | 0.266 | 3.1 |
| 4 | 200 | 23.00 | 11.5 | Average yield: |  |  | 2.7 |
| 5 | 400 | 51.47 | 12.9 |  |  |  |  |
| 6 | 500 | 58.3 | 11.7 |  |  |  |  |
| 7 | 500 | 61.4 | 12.3 |  |  |  |  |
| 8 | 600 | 70.6 | 11.8 |  |  |  |  |
| Average yield: |  | 11.9 |  |  |  |  |  |

Figure 4:
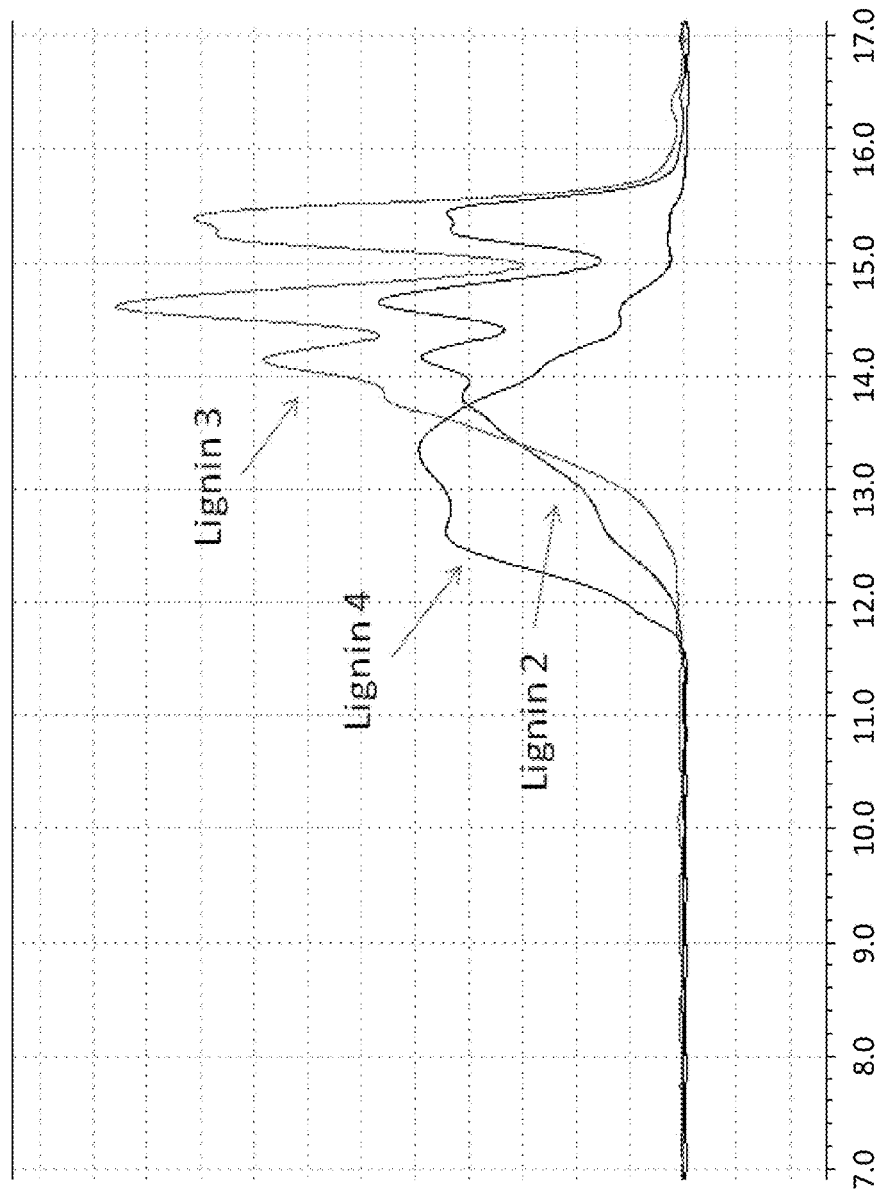
FIG. 4 is a series of GPC traces of various fractions obtained by solvent extraction of the crude candlenut lignin. Lignin 2 is the dichloromethane-treated fraction. Lignin 3 is the ethyl acetate-soluble portion of Lignin 2, and Lignin 4 is the ethyl acetate-insoluble portion of Lignin 2.

The remaining brown colored filter cake (Lignin 2) still displayed a GPC signal over a broad molecular weight range ($M_w$=1054 and dispersity=1.32). Subsequently, several organic solvents were tested for use in fractionation. Ethyl acetate was found to be appropriate for fractionation of Lignin 2 into lighter and heavier components (FIG. 4). The heavier, ethyl acetate insoluble fraction (Lignin 4) displayed an average molecular weight of 2449 g/mol and polydispersity of 1.18. The filtrate, Lignin 3, contained a light brown material after removal of the solvent, and had an average molecular weight of 1133 g/mol, with a polydispersity of 1.175. A summary of the above described procedures is displayed on FIG. 1. A summary of the extraction procedures as well a comparison of GPC traces of the different fractions is shown in FIG. 4. A summary of yields is given in Tables 2 and 12. The details of the GPC analysis are shown in Table 3.

TABLE 3

GPC analysis of the obtained lignin fractions

| Lignin fraction | $M_N$ | $M_w$ | $M_w/M_n$ |
|---|---|---|---|
| Lignin 1 | 862 | 1162 | 1.347 |
| Lignin2 | 797 | 1054 | 1.320 |
| Lignin3 | 736 | 1133 | 1.175 |
| Lignin4 | 1959 | 2449 | 1.18 |
| Oil | 242 | 595 | 1.18 |

Figure 5:
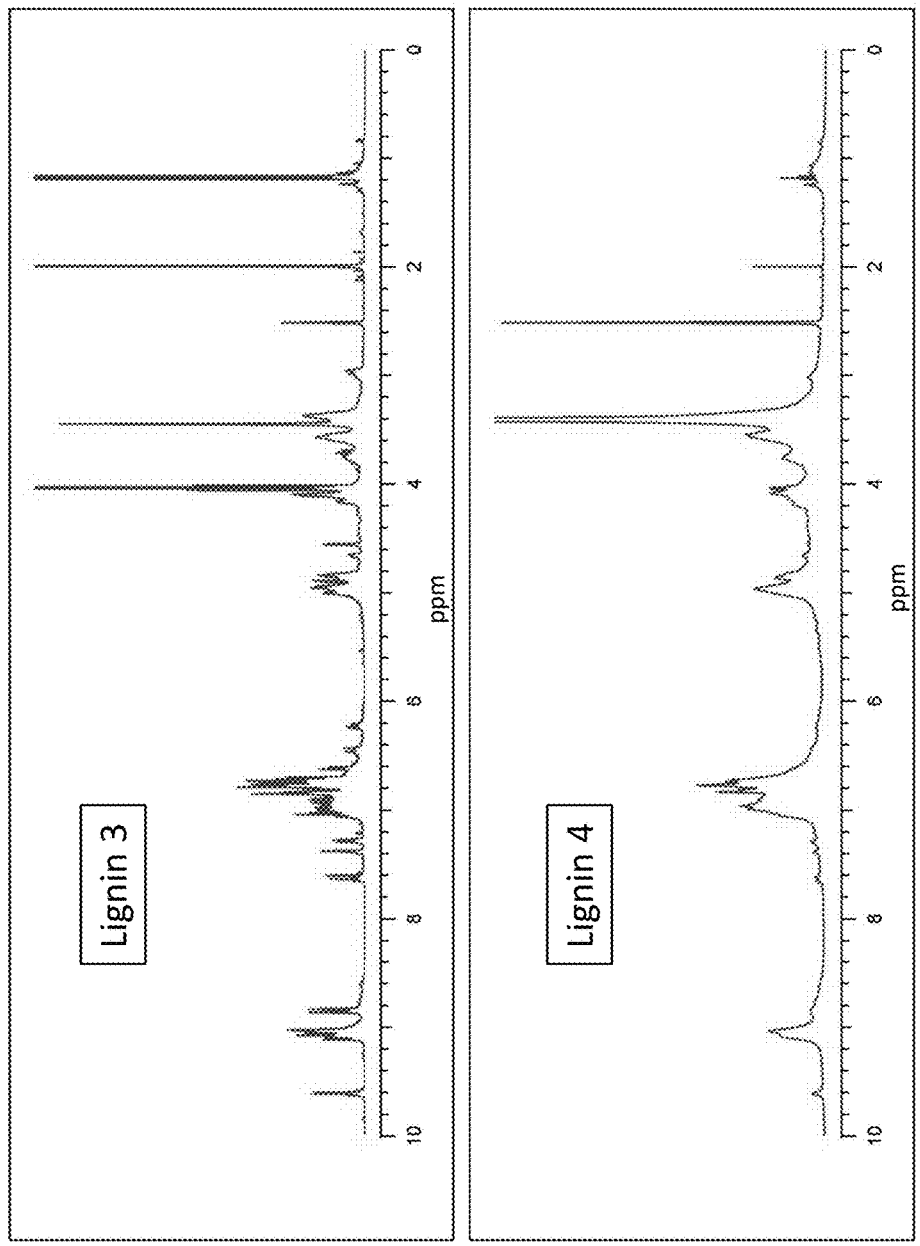
FIG. 5 is a series of $^1$H NMR spectra (500.13 MHz, $CD_3OD$) depicting Lignin 3 (ethyl acetate-soluble) and Lignin 4 (ethyl acetate-insoluble).
Figure 6:
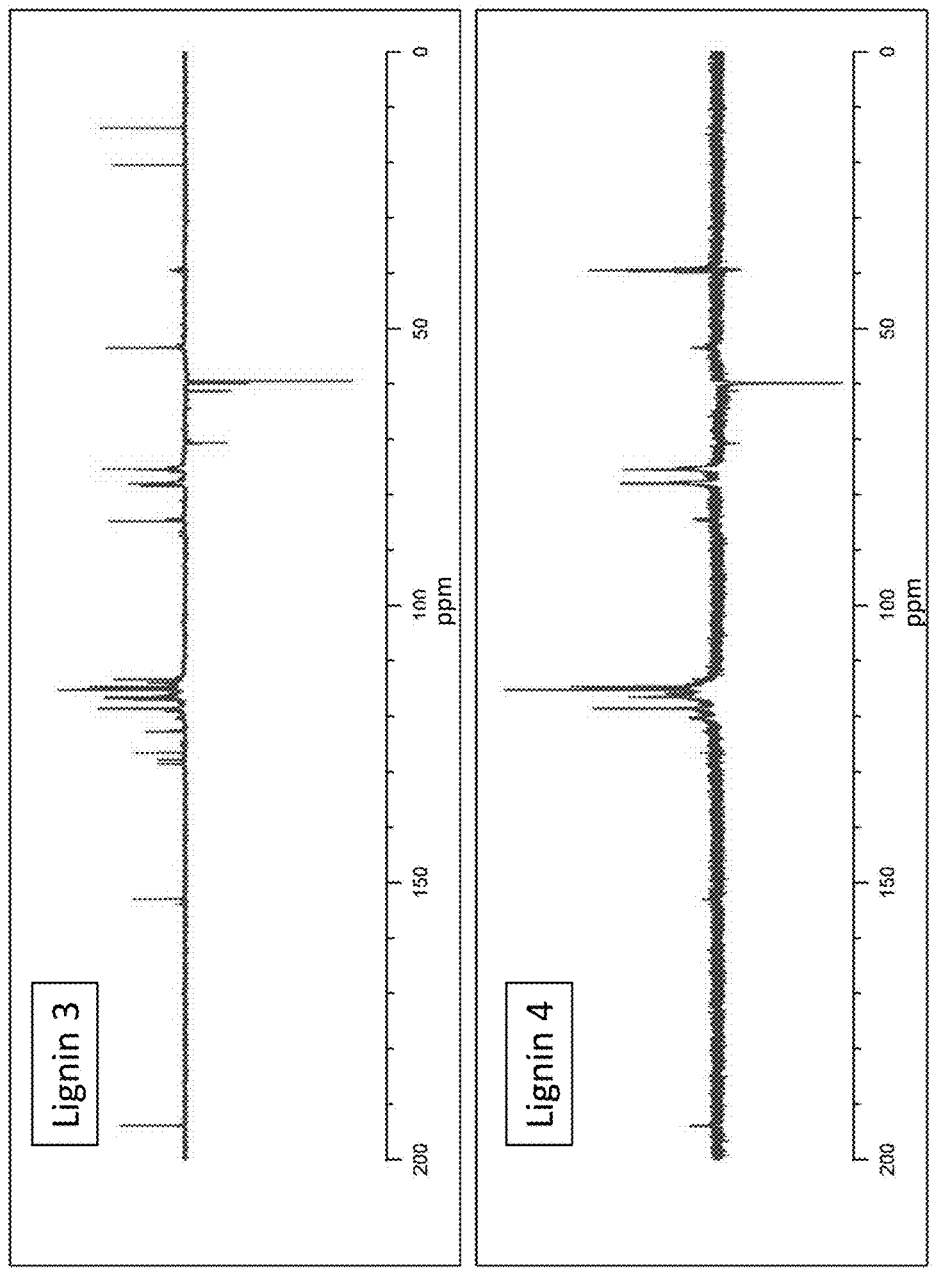
FIG. 6 is a series of $^{13}$C-DEPT-135 NMR spectra (125.76 MHz, DMSO-$d_6$) of Lignin 3 (ethyl acetate-soluble) and Lignin 4 (ethyl acetate-insoluble).

The spectroscopic features of both of the obtained fractions (Lignin 3 and Lignin 4) are similar. The $^1H$ and $^{13}C$ NMR spectra (FIGS. 5 and 6) gave signals with comparable chemical shifts, sharper in the lighter fraction and broader in the heavier fraction, consistently with their size and with the spectra measured for other organosolv lignins.

Synthesis and Characterization of Porous Metal Oxides

Figure 7:
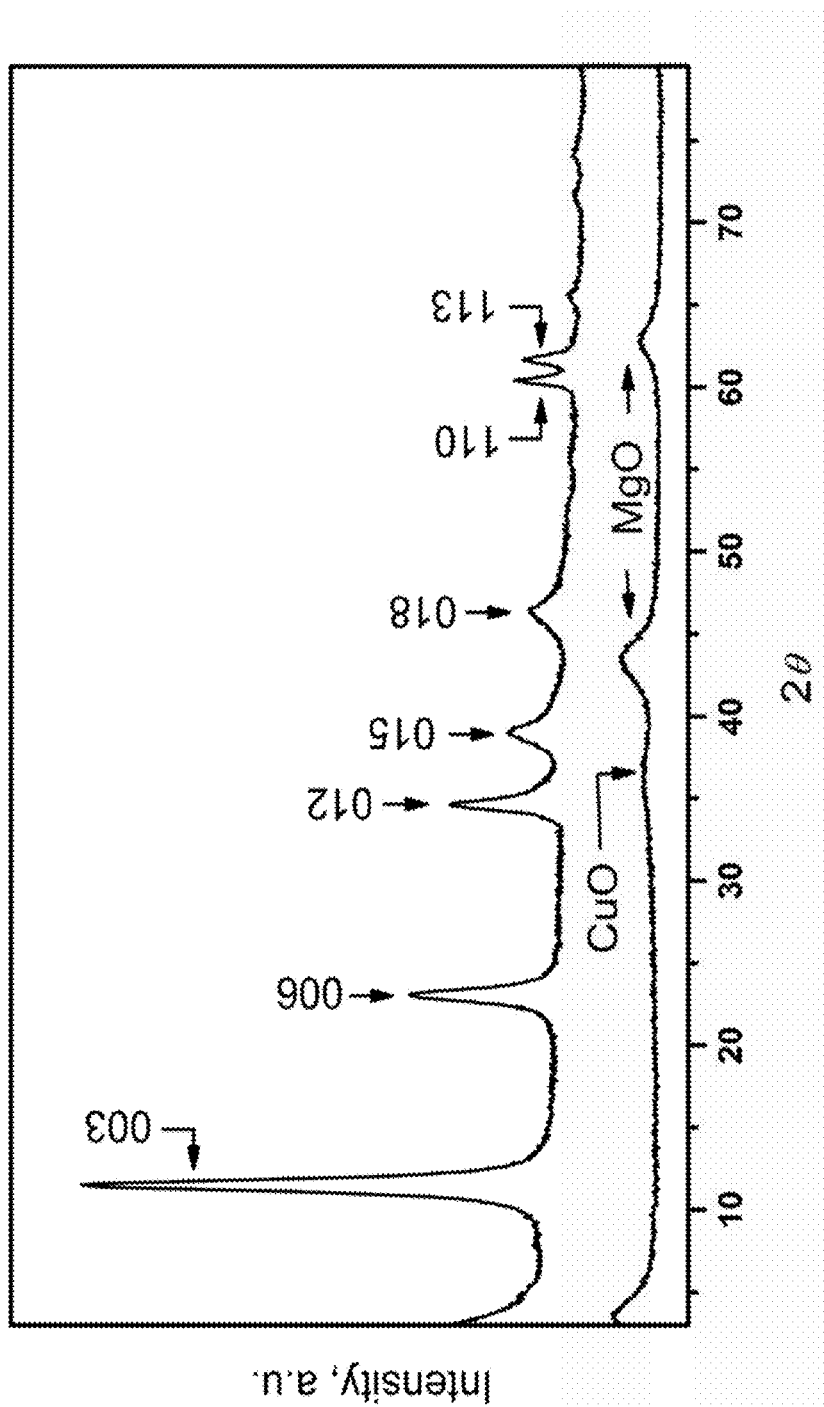
FIG. 7 is a powder XRD spectrum of a representative HTC precursor (top) and the corresponding PMO post-calcination (bottom).

A series of porous metal oxide (PMO) catalysts, were prepared by calcination of hydrotalcite-like (HTC) precursors. These HTC's were prepared by modification of the hydrotalcite structure (Cavani et al., 1991, Catalysis Today 173-301) with a variety of copper and non-copper dopants. The hydrotalcite-like precursors were synthesized by co-precipitation of $Na_2CO_3$ and NaOH with solutions of $Al(NO_3)_3$, $Mg(NO_3)_2$ and suitable metal nitrates. In all synthesized HTCs, a 3:1 molar ratio of $M^{2+}$ with respect to $M^{3+}$ was kept. The first group of HTCs, containing copper, were synthesized by replacing 20 mol % of the $Mg^{2+}$ with $Cu^{2+}$ and additionally replacing 20 mol % of either the $Mg^{2+}$ or the $Al^{3+}$ ions with another dopant. The second group of HTCs does not contain copper, but instead incorporates similar dopants to the first group. The HTC catalyst precursors were analyzed by X-ray powder diffraction (XRPD) which revealed a highly ordered crystalline structure with distinct hydrotalcite-like features consistent with the literature (FIG. 7) (Cavani et al., 1991, Catalysis Today 173-301). After calcination at 460° C. for 24 hours, porous metal oxides (PMOs) of different colors were obtained, and their BET surface area was determined. The composition of the obtained HTC's in addition to the BET surface area of the obtained PMO's is listed in Table 4.

TABLE 4

Chemical composition of obtained HTC's and BET surface area of the PMO's obtained by calcination

| Catalyst code | Metal composition | Molar composition | BET surface area |
|---|---|---|---|
| $Cu_{20}PMO$ | Cu/Mg/Al | 0.03/0.12/0.05 | 142 $m^2/g$ |
| $Cu_{20}Cr_{20}PMO$ | Cu/Mg/Al/Cr | 0.03/0.12/0.04/0.01 | 113 $m^2/g$ |
| $Cu_{20}La_{20}PMO$ | Cu/Mg/Al/La | 0.03/0.12/0.04/0.01 | 161 $m^2/g$ |
| $Cu_{20}Mn_{20}PMO$ | Cu/Mn/Mg/Al | 0.03/0.03/0.09/0.05 | 190 $m^2/g$ |
| [Mg/Al]PMO | Mg/Al | 0.15/0.05 | 68 $m^2/g$ |
| $Cr_{20}PMO$ | Mg/Al/Cr | 0.15/0.04/0.01 | 131 $m^2/g$. |
| $La_{20}PMO$ | Mg/Al/La | 0.15/0.04/0.01 | 53 $m^2/g$ |
| $Zn_{20}PMO$ | Zn/Mg/Al | 0.03/0.12/0.05 | 61. $m^2/g$ |

Depolymerization in Supercritical Methanol

Catalytic runs were performed using Lignin 4, obtained by the extraction procedures described elsewhere herein. In a typical run, 100 mg of PMO catalyst, 100 mg of Lignin 4 and 3 mL methanol were heated in a 10 mL stainless steel bomb to 310° C. After the indicated time intervals, the vessels were rapidly cooled and the liquid phase was separated from the solids after centrifugation and decantation. The products of the liquid phase were obtained upon removal of the solvent. These hydrogenolysis oils were weighed and subsequently a sample of each was taken for GPC analysis. The solids of the reactions were dried and weighed, and biomass conversion was based on gravimetric analysis of these solid residues. The solids were than subjected to a nitric acid test ($HNO_3$ test) to rule out the presence of biochar.

All copper containing catalysts were screened for a reaction time of 40 minutes as well as 1 hour. Shorter reaction times were used because the desired products (aromatic dimers, trimers) were expected to form rapidly under the utilized reaction conditions. The results are summarized in Table 5.

TABLE 5

Products of the liquid phase and biomass conversion at shorter reaction times using a series of Cu doped PMO

| Entry | Time [min] | Catalyst Code | m (bio oil) [g] | m (solids) [g] | Biomass conversion [%] |
|---|---|---|---|---|---|
| 1 | 40 | $Cu_{20}PMO$ | 0.019 | 0.177 | 22.9 |
| 2 | 40 | $Cu_{20}Cr_{20}PMO$ | 0.01 | 0.170 | 30.3 |
| 3 | 40 | $Cu_{20}La_{20}PMO$ | 0.017 | 0.170 | 30.9 |
| 4 | 40 | $Cu_{20}Mn_{20}PMO$ | 0.015 | 0.196 | — |
| 5 | 60 | $Cu_{20}PMO$ | 0.025 | 0.152 | 48.3 |
| 6 | 60 | $Cu_{20}Cr_{20}PMO$ | 0.008 | 0.163 | 36.8 |
| 7 | 60 | $Cu_{20}La_{20}PMO$ | 0.026 | 0.166 | 33.8 |
| 8 | 60 | $Cu_{20}Mn_{20}PMO$ | 0.025 | 0.193 | — |

In all experiments shown in Table 5, the solids were dark in color, indicating unreacted biomass and the absence of char (as determined by the $HNO_3$ test). The results indicated that shorter reaction times were not sufficient to reach full conversion of lignin with any of the examined catalysts. The highest conversion among the tested copper containing catalysts was observed with the $Cu_{20}PMO$. Using Lignin 4 as substrate, the percent conversion was improved from 22.9% in 40 minutes was improved to 48% in 1 hour. (Table 5, Entries 1 and 5). Biomass conversion in all other cases remained 30% within 40 minutes (Table 5, Entries 2 and 3) and 33-36% within 1 hour reaction time (Table 5, Entries 6 and 7). With $Cu_{20}Mn_{20}PMO$, a higher than usual amount of solid residue was obtained, and therefore the combined mass of the products of the liquid phase and solids totaled more than the theoretically expected mass. As a result, these runs were tabulated as having no biomass conversion (Table 5, Entries 4 and 8). Although not wishing to be bound by any particular theory, it is possible that the observed mass increase is due to side reactions involving methanol.

Generally, after the evaporation of solvent (methanol), the products of the liquid phase were brown to light brown oils. The yield of bio-oil was improved slightly from 0.014-0.019 g at 40 minutes to 0.0252-0.0263 g at 1 hour using the copper only catalyst and the lanthanum and manganese doped catalysts (Table 5, Entries 1, 3-5, and 7-8). In experiments using the chromium-containing catalyst ($Cu_{20}Cr_{20}PMO$) only, the yields of bio-oil were 0.01 g in 40 minutes and 0.008 g in 1 hour reaction time (Table 5, Entries 2 and 6, respectively), while the biomass conversion was comparable to the other runs. Although not wishing to be bound by any particular theory, these results suggest that the low yields of bio-oil may be due to oxidative side reactions which result in the formation of gaseous or highly volatile products.

GPC measurements of the liquid phase products were performed to determine the extent of depolymerization and average molecular weight of the products obtained. This technique has been previously used to determine molecular weights of lignin and corresponding fractionation products (Salanti et al., 2010, Microchemical Journal 95:345-352; Ingram et al., 2008, Energy & Fuels 22:614-625; Colombini et al., 2007, Microchemical Journal 85:164-173). The fractionation method used to separate out the lighter lignin components still present in Lignin 2 was critical for the application of this methodology, which concentrated on following molecular weight changes in the product mixtures, and then comparing these changes to the molecular weight of the starting material. When Lignin 4 ($M_w$=2400 g/mol) was used as a substrate, the obtained oligomeric or monomeric components were distinctly detected and quantified. Average molecular weight and nominal mass was readily determined based on calibration curves using polystyrene standards of molecular weights 50000, 30000, 17000, 9000, 5000, 2500, 1000 and 580 g/mol.

Figure 8:
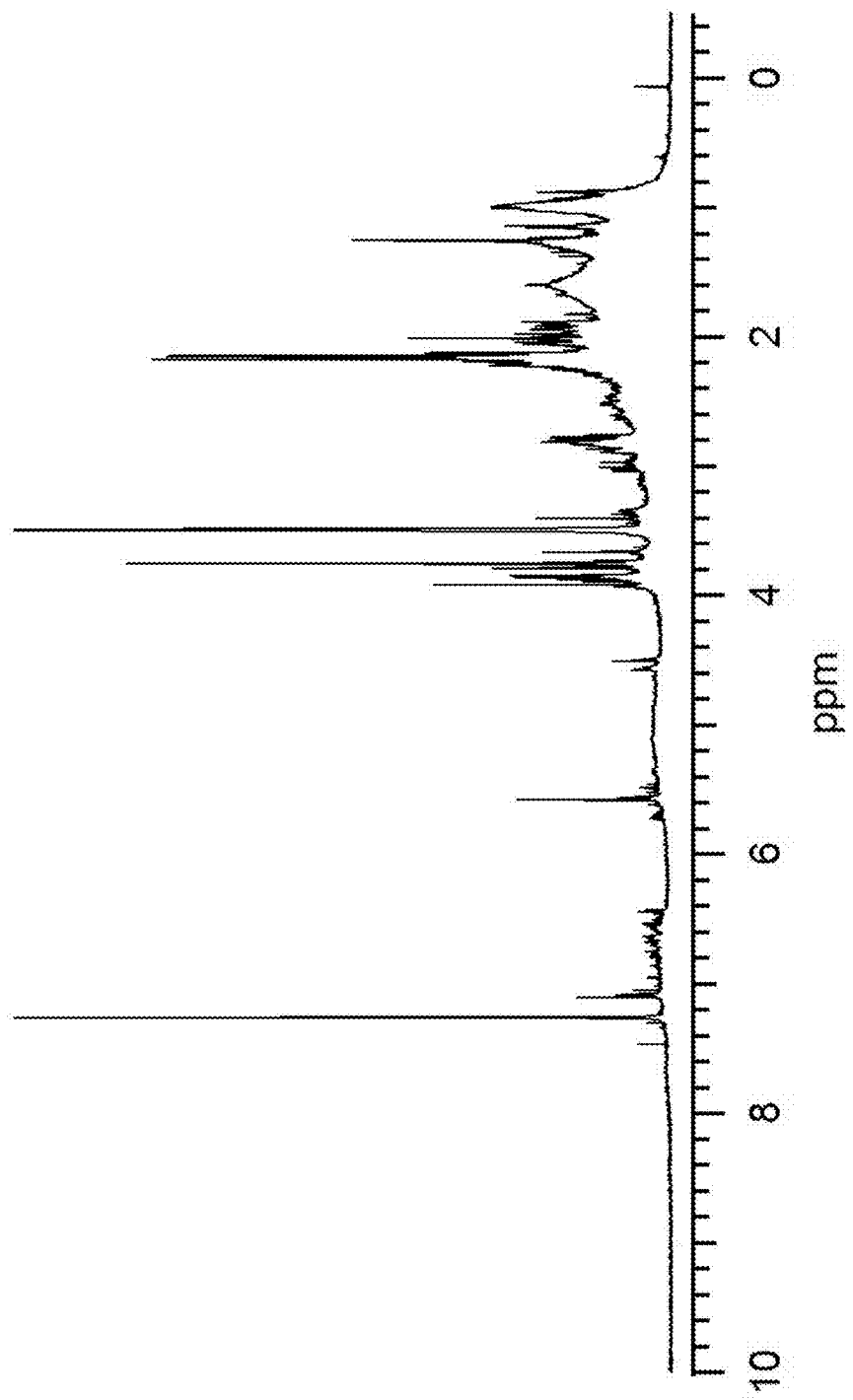
FIG. 8 is a $^1$H NMR spectrum (500.13 MHz, $CDCl_3$) of the product mixture from 100 mg $Cu_{20}La_{10}PMO$ and 100 mg Lignin 4 (ethyl acetate-insoluble lignin), 6 h at 310° C.
Figure 9:
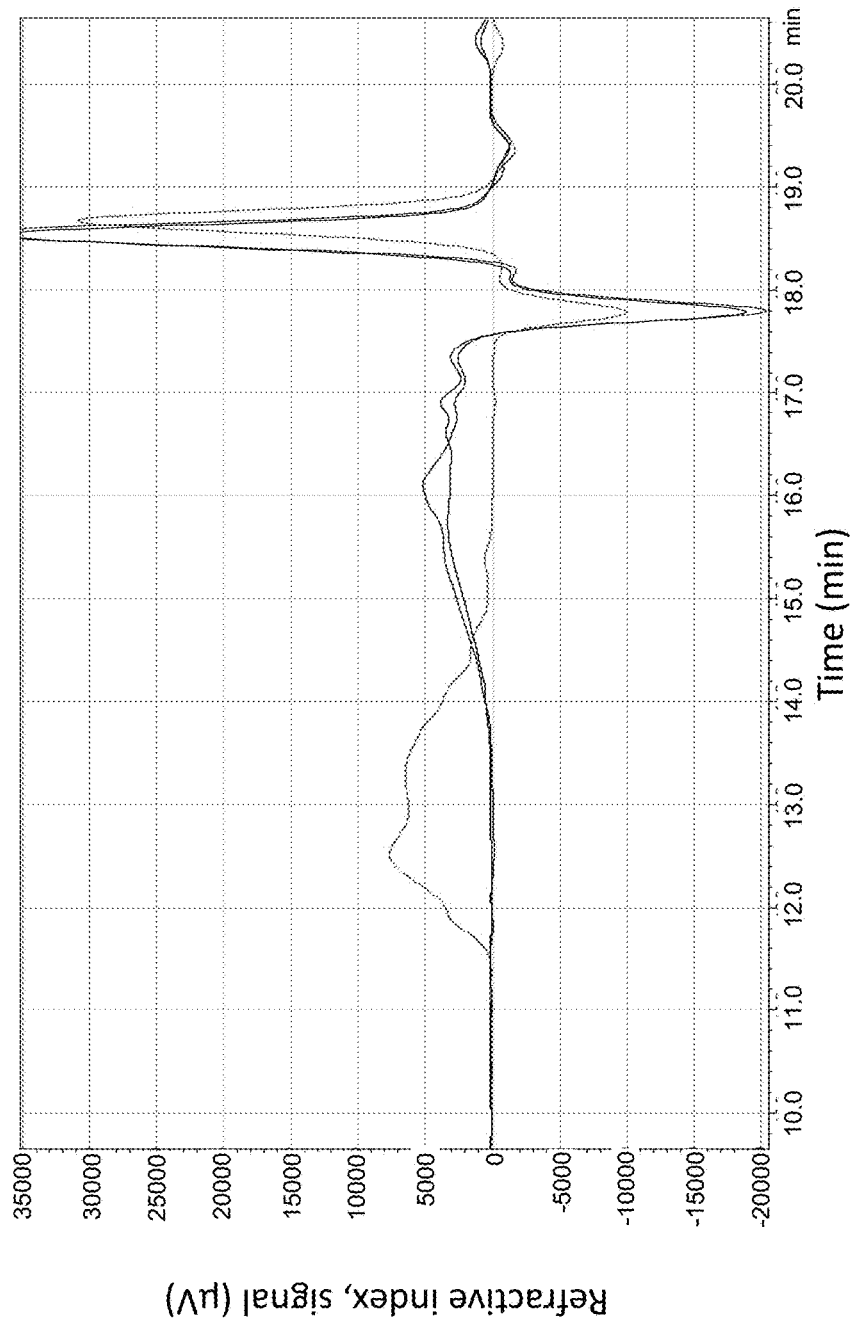
FIG. 9 is a comparison of GPC traces of Lignin 4 (ethyl acetate-insoluble lignin; purple trace) and representative product mixtures (blue and black traces) from treatment with CuPMOs under supercritical conditions.

Liquid phase products from Table 5 were analyzed by GPC, and the results are summarized in Table 6. Sample GPC traces of the product mixtures generated are shown in FIG. 8. Degradation of the starting 2100 g/mol biopolymer to oligomers and monomers successfully occurred, even at short reaction times (40-60 min).

TABLE 6

GPC Analysis of the Liquid Phase Products with Various Copper-Doped PMO

| Entry | Time (min) | Catalyst Code | $M_n$ | $M_w$ | $M_w/M_n$ | % | $M_N$ | % |
|---|---|---|---|---|---|---|---|---|
| 1 | 40 | $Cu_{20}PMO$ | 385 | 509 | 1.322 | 39.4 | 100 | 60.6 |
| 2 | 40 | $Cu_{20}Cr_{20}PMO$ | 375 | 483 | 1.288 | 45.2 | 101 | 54.8 |
| 3 | 40 | $Cu_{20}La_{20}PMO$ | 402 | 524 | 1.30 | 44.3 | 100 | 55.7 |
| 4 | 40 | $Cu_{20}Mn_{20}PMO$ | 378 | 474 | 1.254 | 42.7 | 100 | 57.3 |
| 5 | 60 | $Cu_{20}PMO$ | 366 | 536 | 1.464 | 54.6 | 99 | 45.4 |
| 6 | 60 | $Cu_{20}Cr_{20}PMO$ | 367 | 575 | 1.566 | 49.6 | 98 | 50.4 |
| 7 | 60 | $Cu_{20}La_{20}PMO$ | 390 | 509 | 1.305 | 49.0 | 98 | 51 |
| 8 | 60 | $Cu_{20}Mn_{20}PMO$ | 395 | 509 | 1.278 | 43.2 | 98 | 56.8 |

All applied catalysts showed similar performance in terms of molecular weight distribution. Nominal mass and average molecular weight remained in a similar range independently of reaction time and composition of the catalyst utilized. Lignin 4, which has an average molecular weight of 2100 g/mol, was converted to oligomers with nominal mass ranging from 366 to 402 g/mol and average molecular weight ranging from 474 to 575 g/mol. This corresponds to products containing 3 to 5 aromatic units compared to the starting material that in average contains about 15 monomeric building blocks. Polydispersity in all these runs was between 1.254 and 1.566. About half of the liquid phase products were monomers, which were not analyzed further. For further studies, the lanthanum-doped $Cu_{20}La_{20}PMO$ catalyst was selected.

To evaluate whether conversion and liquid phase product yield could be improved, runs of 2 to 10 hours reaction time were performed with the selected $Cu_{20}La_{20}PMO$. The results, listed in Table 7 indicated that biomass conversion could be significantly improved, with almost complete conversion after 6 hours of reaction time. Biomass conversion gradually improved from 57% at 2 hours (Table 7, Entry 1) to 68% at 3 hours and 72% at 4 hours (Table 7, Entries 2-3, respectively). At 6 hours, a 98.2% biomass conversion was attained. Bio-oil yield increased from 0.0351 g at 2 hours (Table 7, Entry 1) to 0.0577 g at 10 hours, almost attaining the theoretical maximum conversion. Product distribution in terms of average molecular weight showed no significant changes with increasing reaction time, according to GPC measurements (Table 7, Entries 1-6). It was also examined whether aromatic content vs. aliphatic content of the bio-oils changes at lengthy reaction times. $^1$H NMR measurements indicate more signals in the aliphatic region (FIG. 8).

TABLE 7

Catalytic Reactions at Varying Reaction Times using $Cu_{20}La_{20}PMO$

| Entry | Time (h) | m [liquid phase] (g) | m [solids] (g) | Conv % | Mw | Mn | PI | % |
|---|---|---|---|---|---|---|---|---|
| 1 | 2 | 0.0351 | 0.1423 | 57.7 | 372 | 500 | 1.3441 | 54.6 |
| 2 | 3 | 0.042 | 0.132 | 68.0 | 363 | 468 | 1.2893 | 43.1 |
| 3 | 4 | 0.0491 | 0.1276 | 72.4 | 354 | 455 | 1.2853 | 48.6 |
| 4 | 6 | 0.0552 | 0.1018 | 98.2 | 390 | 524 | 1.3436 | 46.2 |
| 6 | 10 | 0.0577 | 0.1044 | 95.6 | 381 | 508 | 1.333 | 44.8 |

Catalysts not containing copper were tested and the liquid product yields, as well as the molecular weight range of the products found, were consistent with the findings of Lercher and coworkers who described base catalyzed mild depolymerization of lignin using sodium hydroxide (Roberts et al., 2011, Chem. Eur. J. 17:5939-5948). The results and catalysts used are summarized in Table 8. The plain [MgAl] PMO performed the best, resulting in 55% biomass conversion after 2 hours and 74.6% conversion after 5 hours. However, these yields are lower than the observed yields using copper-containing catalysts, where full conversion was achieved in 6 hours. $La_{20}PMO$, also reported to promote transesterification due to its increased basicity (Macala et al., 2008, Catalysis Lett. 122:205-209), displayed lower yields, resulting in 38% conversion in 2 hours and 56.8% conversion in 5 hours.

Very little bio-oil yield was obtained with the $Cr_{20}PMO$, as was the case with its copper-doped analogue. This result supports the hypothesis that chromium-containing PMOs promote different type of reactivity, leading to mainly volatile products. Conversion with this catalyst also remained consistently low, with 31.1% and 37.3% conversion in 2 hours and 5 hours reaction time, respectively. In this particular case, the solids analysis showed char formation. Although not wishing to be bound by any particular theory, it is possible that catalyst deactivation might be the reason for low biomass conversion. About 20 mg bio-oil was obtained with all the other catalyst tested within 2 hours, which was improved to 25.5-41.9 milligrams with 5 hours of reaction time. These are slightly lower yields than those obtained with copper doped catalysts. It was hypothesized that depolymerization in the presence of copper is the preferred reaction method.

TABLE 8

Biomass Conversion and Bio-Oil Yields using PMO Not Containing Copper

| Entry | Time (min) | Catalyst Code | m [liquid phase] (g) | m [solids] (g) | Biomass conv % | $M_N$ | $M_W$ | PI | % |
|---|---|---|---|---|---|---|---|---|---|
| 1 | 2 | [Mg/Al]PMO | 0.0199 | 0.145 | 55 | 431 | 637 | 1.478 | 52.4 |
| 2 | 2 | $Zn_{20}$PMO | 0.0253 | 0.1531 | 46.9 | 426 | 562 | 1.319 | 56.9 |
| 3 | 2 | $La_{20}$PMO | 0.0173 | 0.1618 | 38.2 | 437 | 570 | 1.304 | 49.8 |
| 4 | 2 | $Cr_{20}$PMO | 0.0072 | 0.1689 | 31.1 | 372 | 449 | 1.207 | 54.0 |
| 5 | 5 | [Mg/Al]PMO | 0.0341 | 0.1254 | 74.6 | 573 | 759 | 1.32 | 26.9 |
| 6 | 5 | $Zn_{20}$PMO | 0.0419 | 0.1312 | 68.8 | 713 | 981 | 1.375 | 40.1 |
| 7 | 5 | $La_{20}$PMO | 0.0255 | 0.1432 | 56.8 | 576 | 782 | 1.358 | 42.9 |
| 8 | 5 | $Cr_{20}$PMO | 0.0069 | 0.1627 | 37.3 | 554 | 685 | 1.237 | 31.4 |

The average molecular weights of the liquid phase products obtained when using non-copper containing catalysts were found to be higher than those observed when using copper containing catalysts. Interestingly, the average molecular weight increased with longer reaction times, possibly due to condensation processes involving the formed oligomers. Although not wishing to be bound by any particular theory, the reaction conditions supplied by the copper-doped catalysts due to methanol reforming and possibly other types of reactivity seemed to prevent oligomerizations of these reactive intermediates.

Although catalyst screening revealed some differences in the reactivity of Lignin 4 over copper and non-copper containing catalysts in supercritical methanol, the products of the liquid phase were a mixture of monomers and oligomers, wherein the average molecular weights of each component of the mixture did not strongly differ from each other. $^1$H NMR spectroscopy also showed that regardless of the dopant used, hydrogenation of the aromatics could not be completely suppressed in the supercritical regime. Nonetheless, good to excellent bio-oil yields were obtained, and the product mixtures generated were within the desired molecular weight range.

Depolymerization in Liquid Phase with the Introduction of Hydrogen Gas

It was observed that performing the depolymerization reaction under subcritical conditions, i.e. at milder pressures and temperatures, improved the selectivity of the reaction. A set of experiments was conducted using Lignin 3, the lighter molecular weight lignin fraction obtained after fractionation. Lignin 3 was completely soluble in the amount of methanol used in the experiments. The experiments were conducted at temperatures ranging from 220° C. to 140° C. using various amounts of [Mg/Al]PMO and $Cu_{20}$PMO, with hydrogen gas added to the vessel at room temperature to an initial pressure of 40 bar.

TABLE 9

Reaction Conditions for Mild Depolymerization of Lignin 3 using $Cu_{20}$PMO and [Mg/Al]PMO

| Entry | Catalyst Code | M (lignin 3) [g] | M (PMO) [g] | T [h] | T [° C.] | m [liquid phase] [g] | m [solids] [g] | Biomass conv % |
|---|---|---|---|---|---|---|---|---|
| 1 | $Cu_{20}$PMO | 1 | 0.5 | 8 | 220 | 0.468 | 0.844 | 65.6 |
| 2 | [Mg/Al]PMO | 1 | 0.5 | 18 | 220 | 0.1842 | 1.1274 | 37.26 |
| 3 | $Cu_{20}$PMO | 1 | 0.5 | 18 | 180 | 0.7122 | 0.5751 | 92.5 |
| 4 | $Cu_{20}$PMO | 5 | 3 | 18 | 180 | 2.48 | 4.1795 | 76.41 |
| 5 | $Cu_{20}$PMO | 2 | 1 | 20 | 140 | 0.9092 | 1.810 | 60.5 |
| 6 | $Cu_{20}$PMO | 4 | 1 | 18 | 180 | 1.6563 | 3.6964 | 67.41 |
| 7 | *$Cu_{20}$PMO | 1 | 1 | 12 | 180 | 0.1594 | 1.7673 | 23.27 |

General conditions: 30 ml methanol, 40 bar $H_2$ initial pressure
*no $H_2$ gas added In Entry 1 of Table 9, a 100 ml Parr reactor was charged with 30 ml methanol, 1 gram Lignin 3, and 0.5 g $Cu_{20}$PMO, and the reaction vessel was pressurized with 40 bars of hydrogen at room temperature. The vessel was heated to 220° C. for 8 hours. A colorless solution was obtained that quickly turned brown upon exposure to air. The solids turned brownish in color when subjected to the $HNO_3$ test, indicating the absence of char. High liquid phase product yield (0.468 g) was observed upon removal the solvent. In contrast, when the same experiment was repeated with [Mg/Al]PMO (not containing any copper) for 18 hours, the bio-oil yield was significantly lower (0.1842 g) and was found to be a complex product mixture. The major side product was dark, degraded lignin and biochar, both covering the bottom of the reactor (1.842 g solids in total) (Table 9, Entry 2). A different control experiment using $Cu_{20}$PMO only in the absence of hydrogen gas (Table 9, Entry 7) also resulted in low conversion (23%) and low bio-oil yields, similar to those observed in Entry 2 of Table 9.

In subsequent experiments examining reaction conditions, it was observed that almost complete biomass conversion and very high product yields (0.7122 g) could be achieved at 180° C. using 1 g lignin and 0.5 g $Cu_{20}$PMO (Table 9, Entry 3). Increasing the lignin loading as high as 5 g, and increasing catalyst loading to 3 g, resulted in 76.41% conversion and 2.48 g product yield at 180° C. in 18 hours (Table 9, Entry 4). With a lignin to catalyst ratio of 4:1, a 67.4% conversion was attained, with 1.656 g of recovered product (Table 9, Entry 6). Even at a reaction temperature as low as 140° C., biomass conversion was still 60.5% with 0.902 g of obtained product (Table 9, Entry 5). Based on these results, it was observed that the use of $Cu_{20}PMO$ in the presence of $H_2$ gas results in high yields of the liquid phase products in addition to full biomass conversion.

Identification of the Liquid Phase Products

Figure 10:
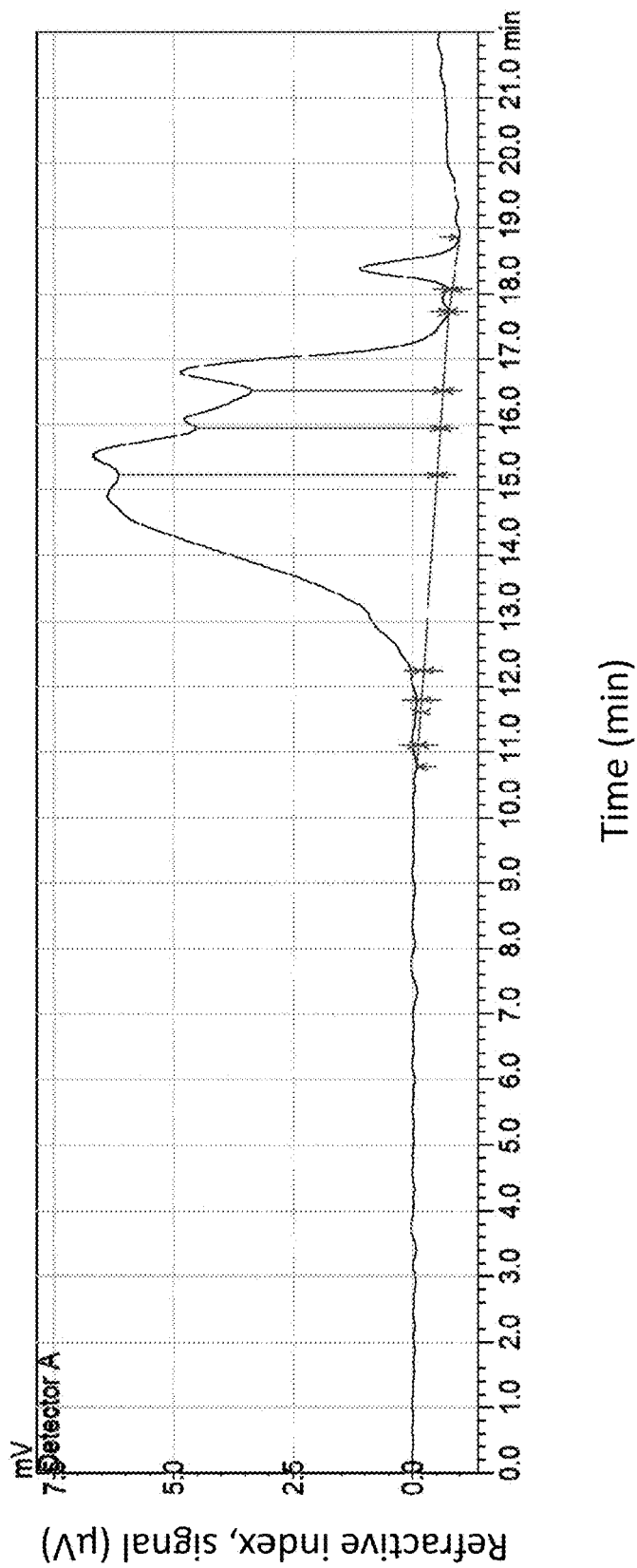
FIG. 10 is a GPC trace depicting products using 0.5 g Mg/Al PMO and 1 g lignin at 220° C.
Figure 11:
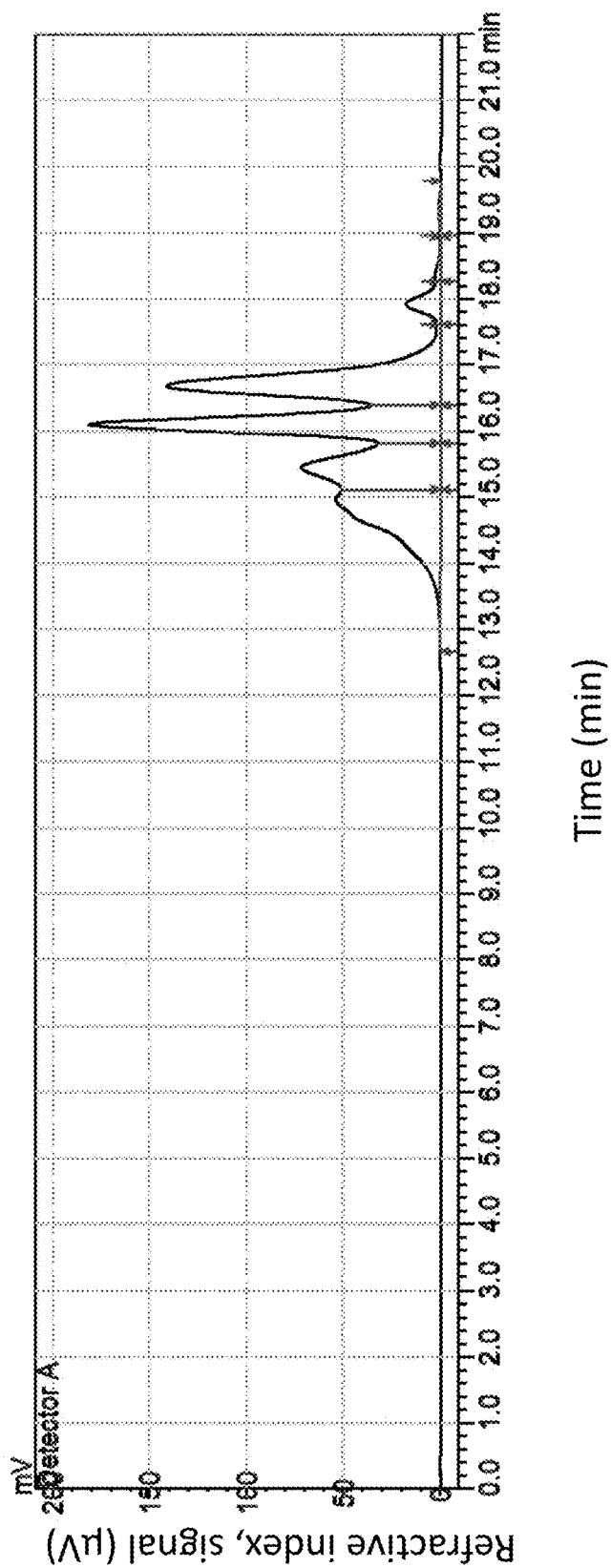
FIG. 11 is a GPC trace depicting products using 0.5 g $Cu_{20}PMO$ and 1 g lignin at 220° C.
Figure 12:
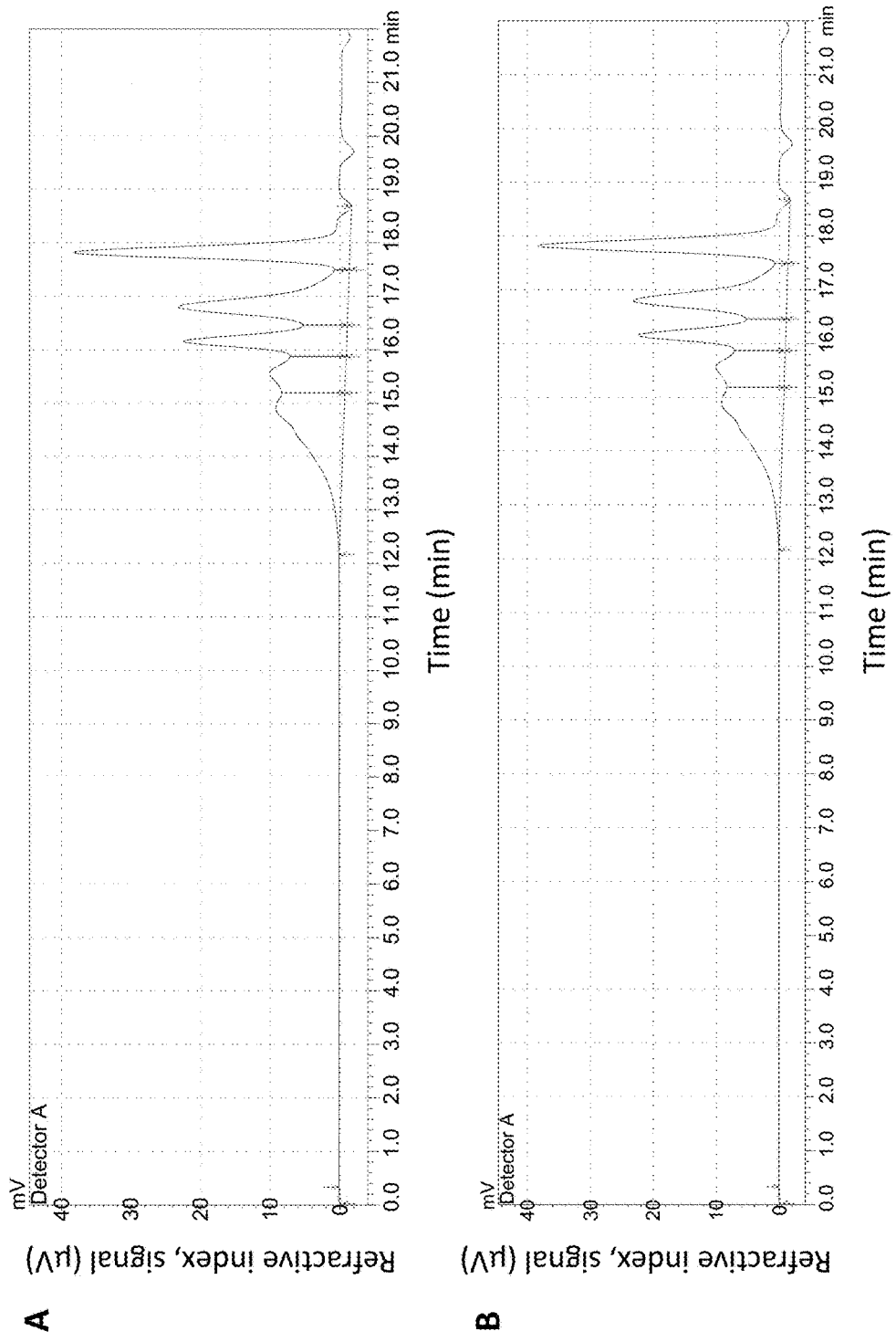
FIG. 12, comprised of FIGS. 12A-12B, depicts GPC traces of products of mild depolymerization in the liquid phase.

In sharp contrast to the runs in supercritical methanol, where product mixtures do not significantly differ in terms of molecular weight distribution, a clear difference was seen in the subcritical runs. A comparison of the GPC traces of the products of Table 9, Entry 1 and Entry 2 is shown in FIGS. 10 and 11. When $Cu_{20}PMO$ was used, the GPC trace indicated sharp signals in the Mw range. However, this was not the case with Mg/Al PMO, wherein the product distribution resembles that of the supercritical runs.

Figure 13:
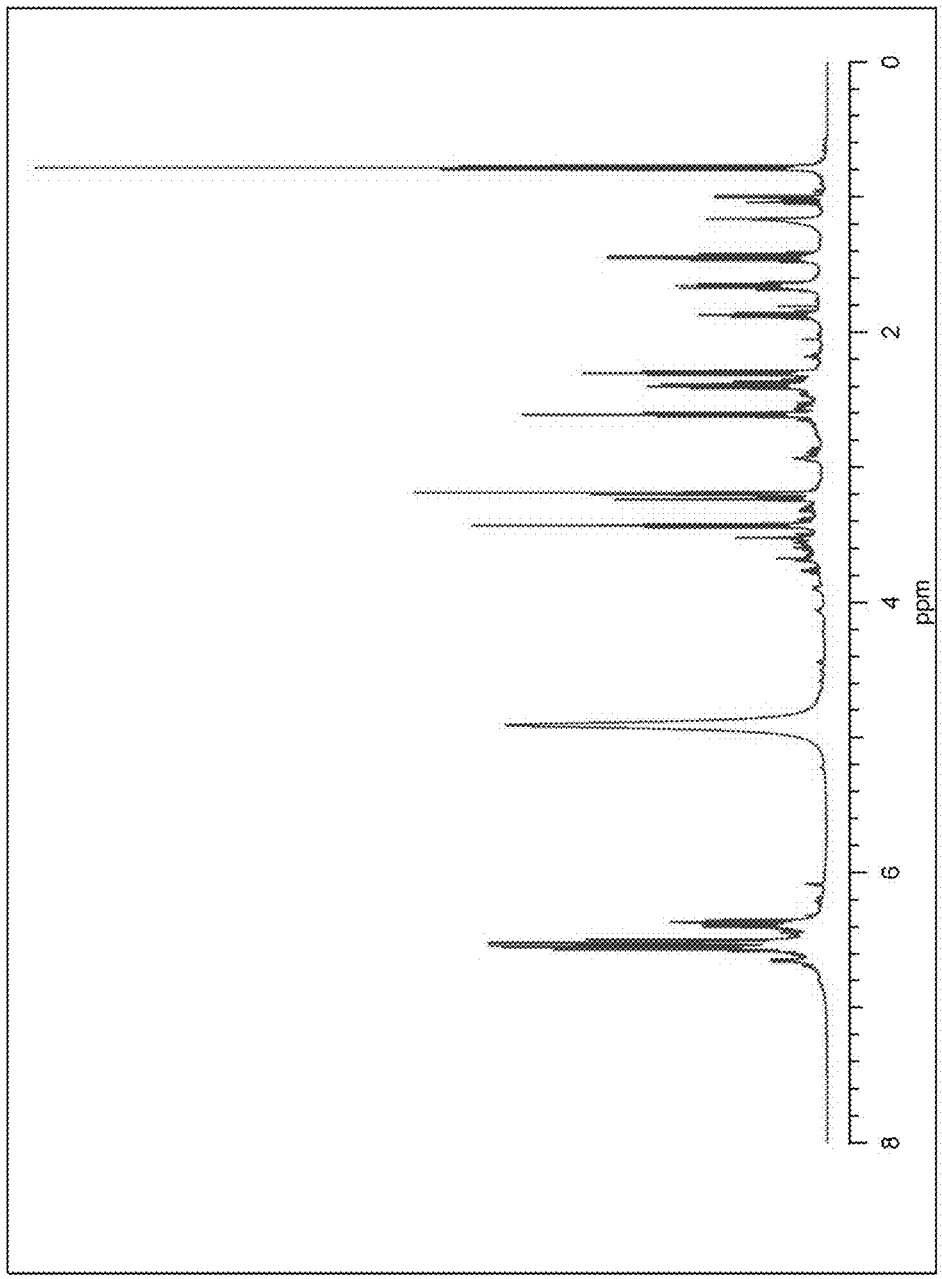
FIG. 13 is a $^1$H NMR spectrum depicting crude reaction products using 4 g lignin, 1 g $Cu_{20}PMO$, initial pressure of 40 bar $H_2$ and 180° C.
Figure 14:
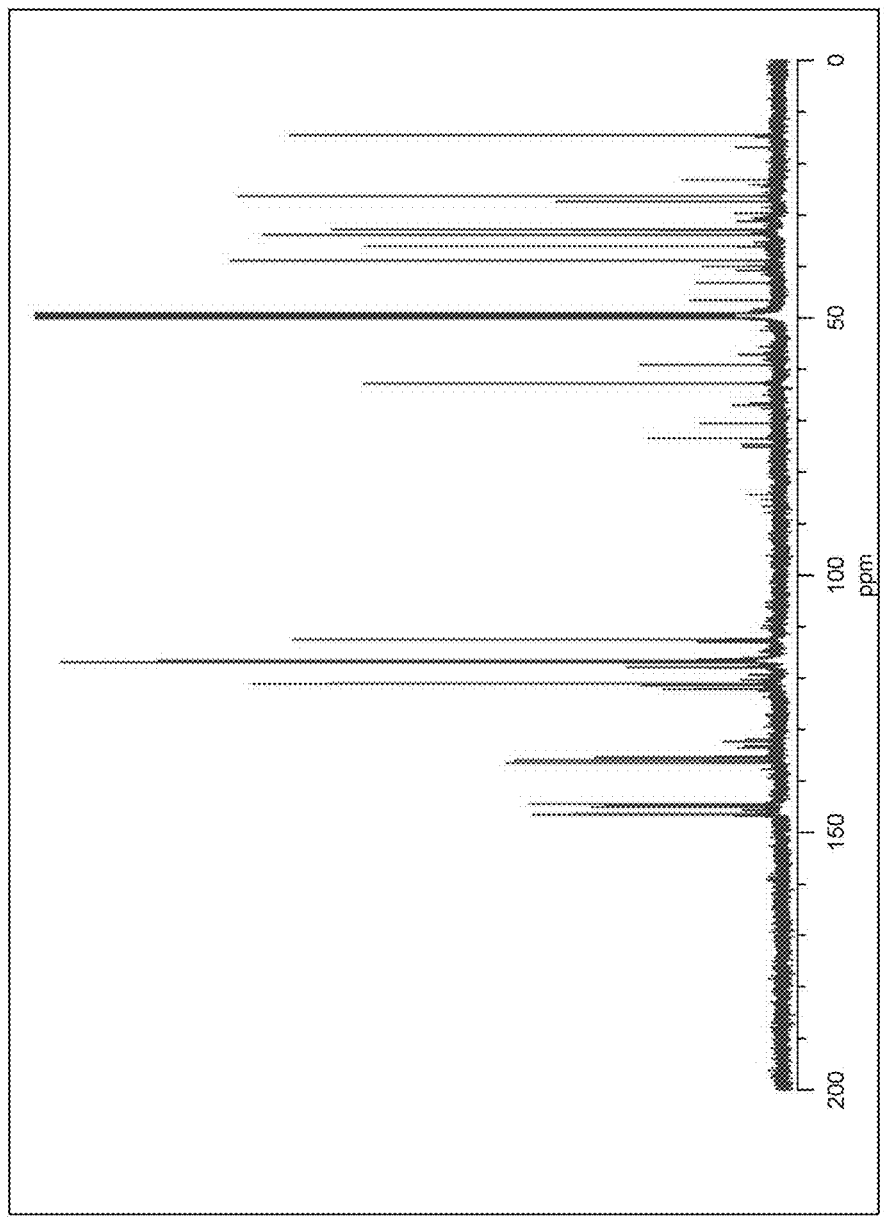
FIG. 14 is a $^{13}$C NMR spectrum depicting crude reaction products using 4 g lignin, 1 g $Cu_{20}PMO$, initial pressure of 40 bar $H_2$ and 180° C.
Figure 15:
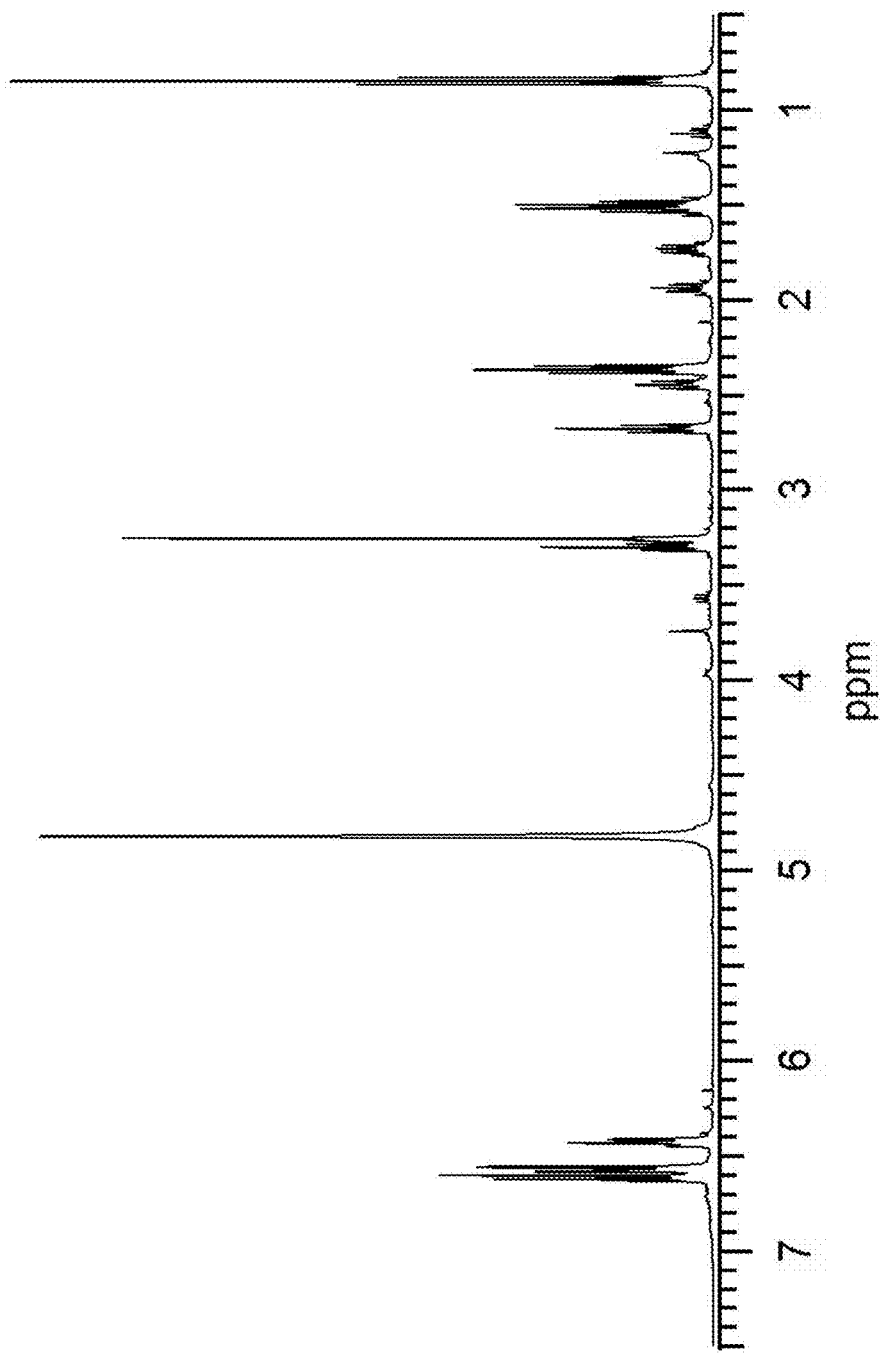
FIG. 15 is a $^1$H NMR spectrum depicting products of Column 1, Fractions 3-7.
Figure 16:
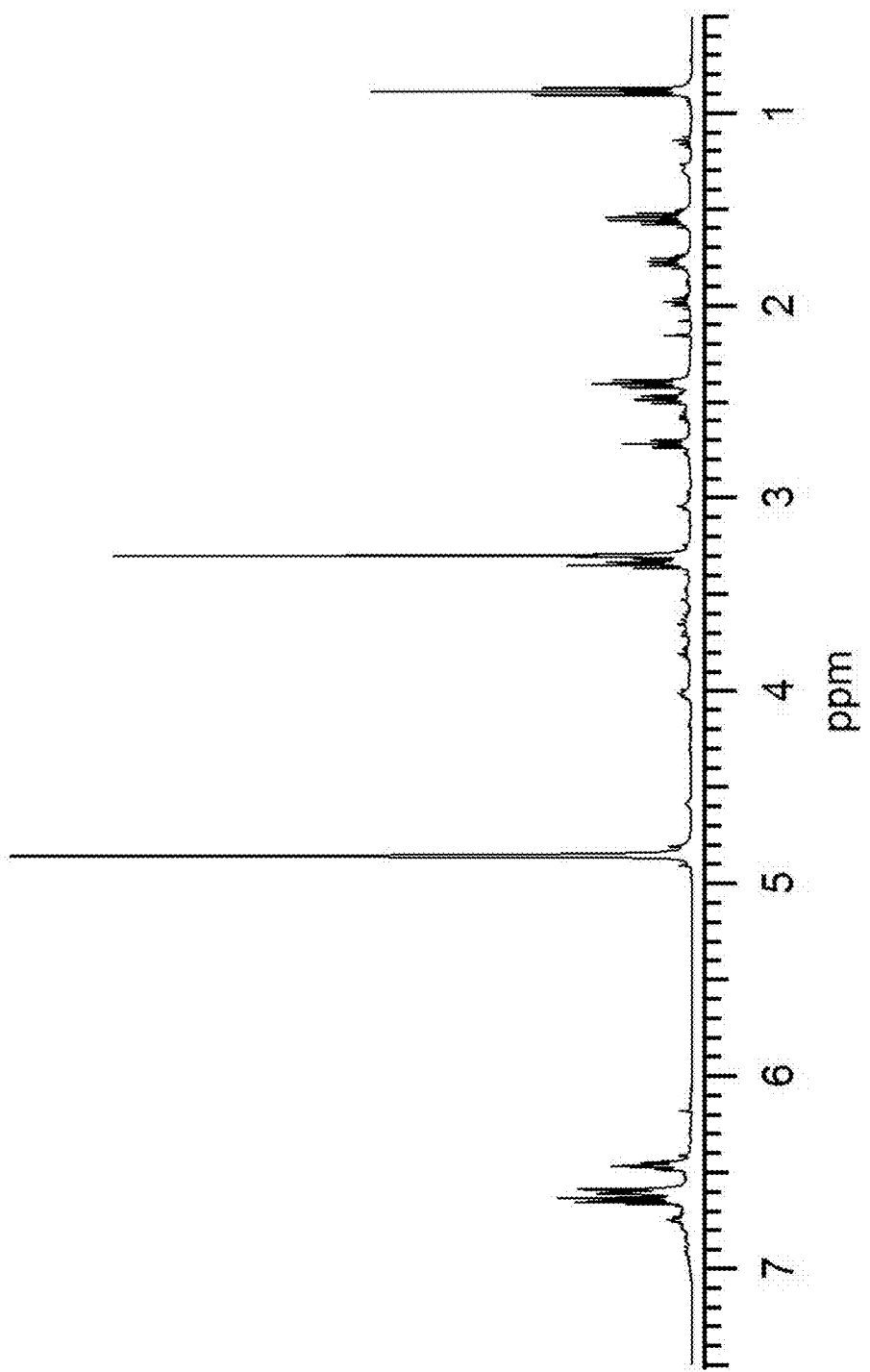
FIG. 16 is a $^1$H NMR spectrum depicting products of Column 1, Fractions 8-14.
Figure 17:
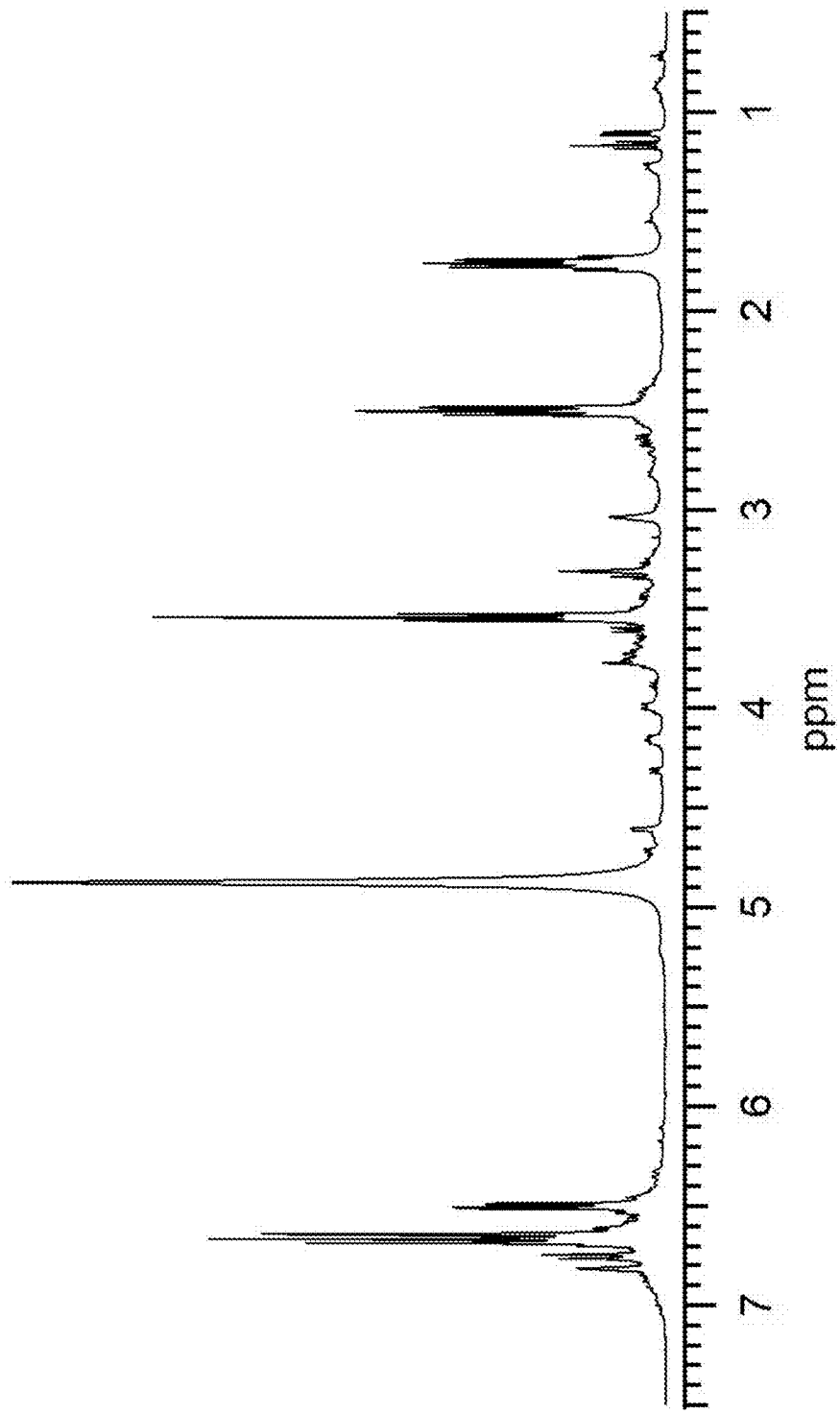
FIG. 17 is a $^1$H NMR spectrum depicting products of Column 1, Fractions 14-20.
Figure 18:
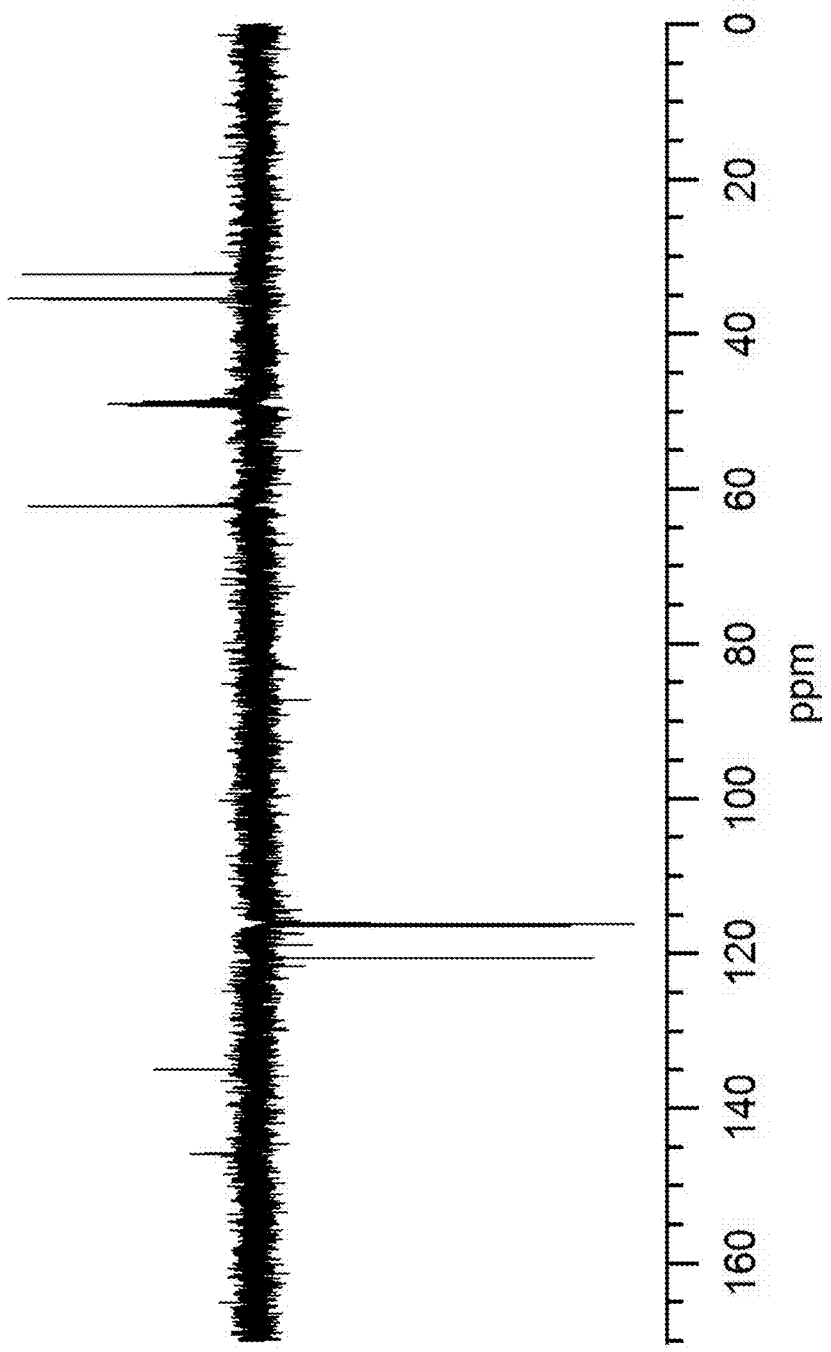
FIG. 18 is a $^{13}$C NMR spectrum depicting spectrum of products of Column 1, Fractions 14-20.
Figure 19:
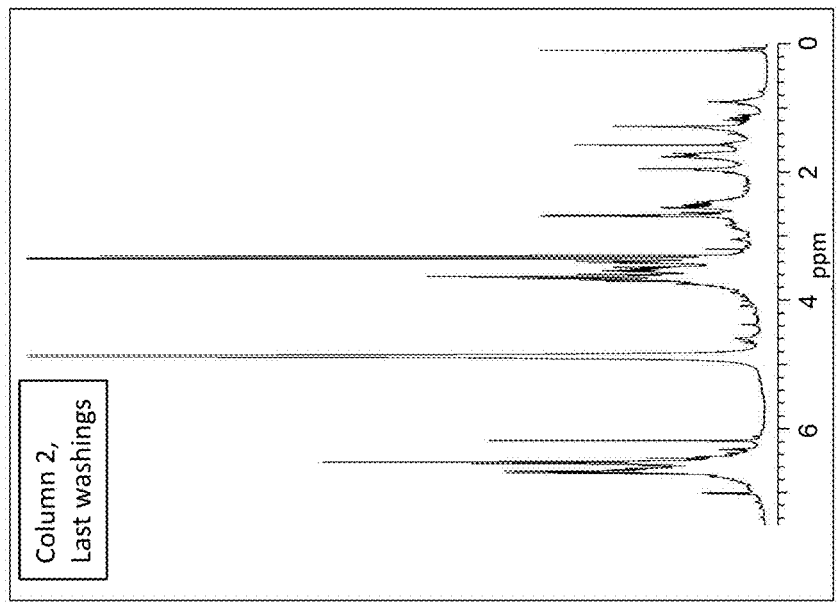
FIG. 19 is a $^1$H NMR spectrum depicting Column 2, last fractions.
Figure 20:
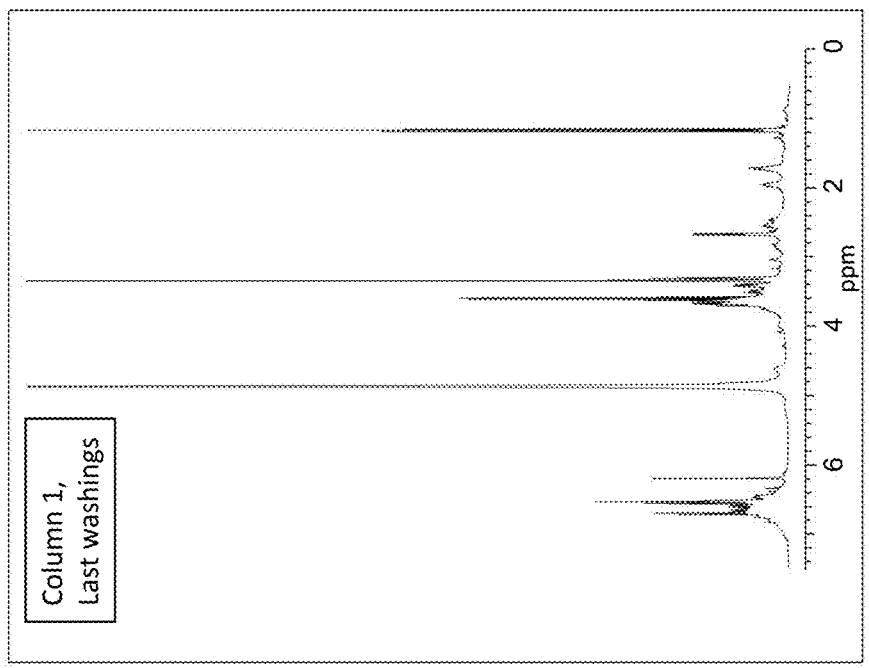
FIG. 20 is a $^1$H NMR spectrum depicting Column 1, last fractions.
Figure 21:
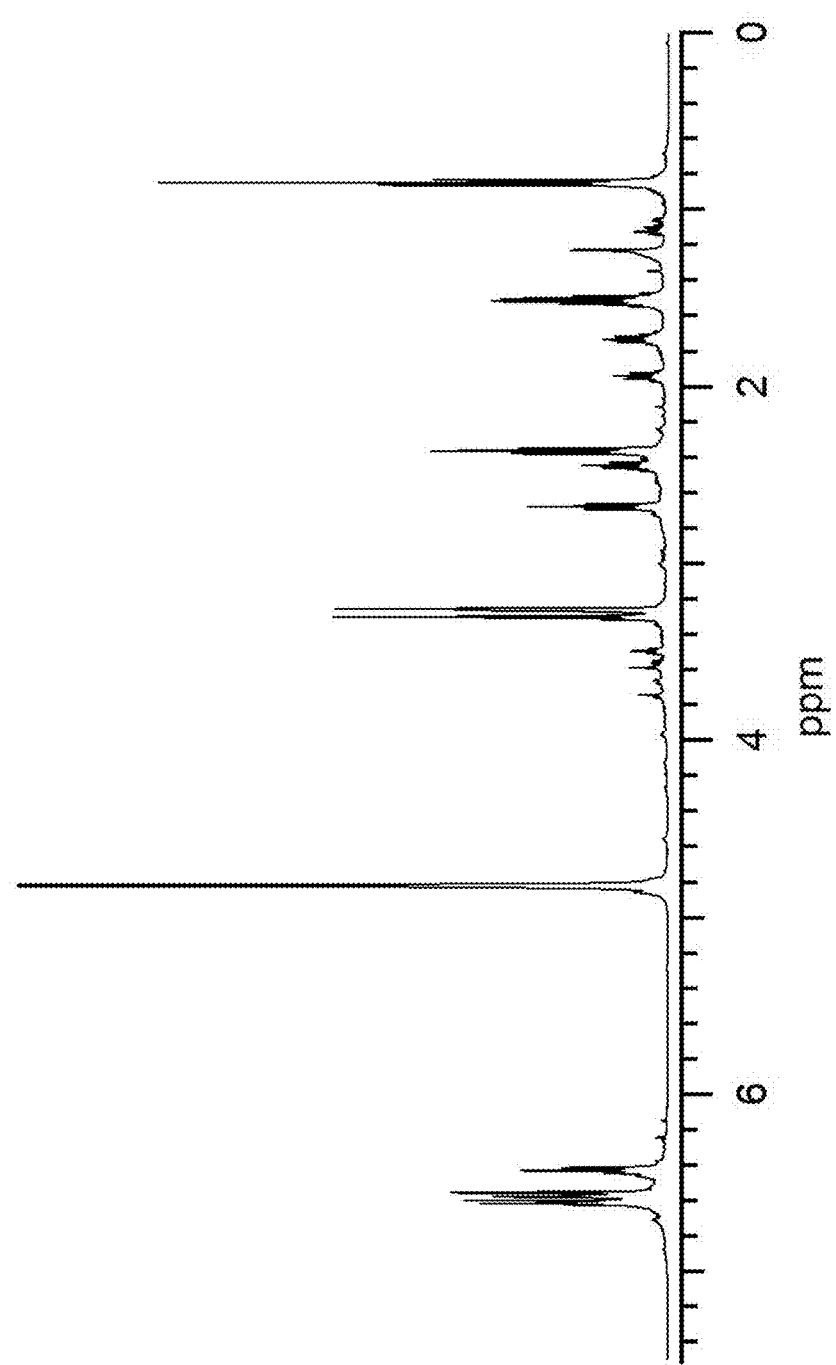
FIG. 21 is a $^1$H NMR spectrum depicting products of Column 2, fractions 1-3.
Figure 22:
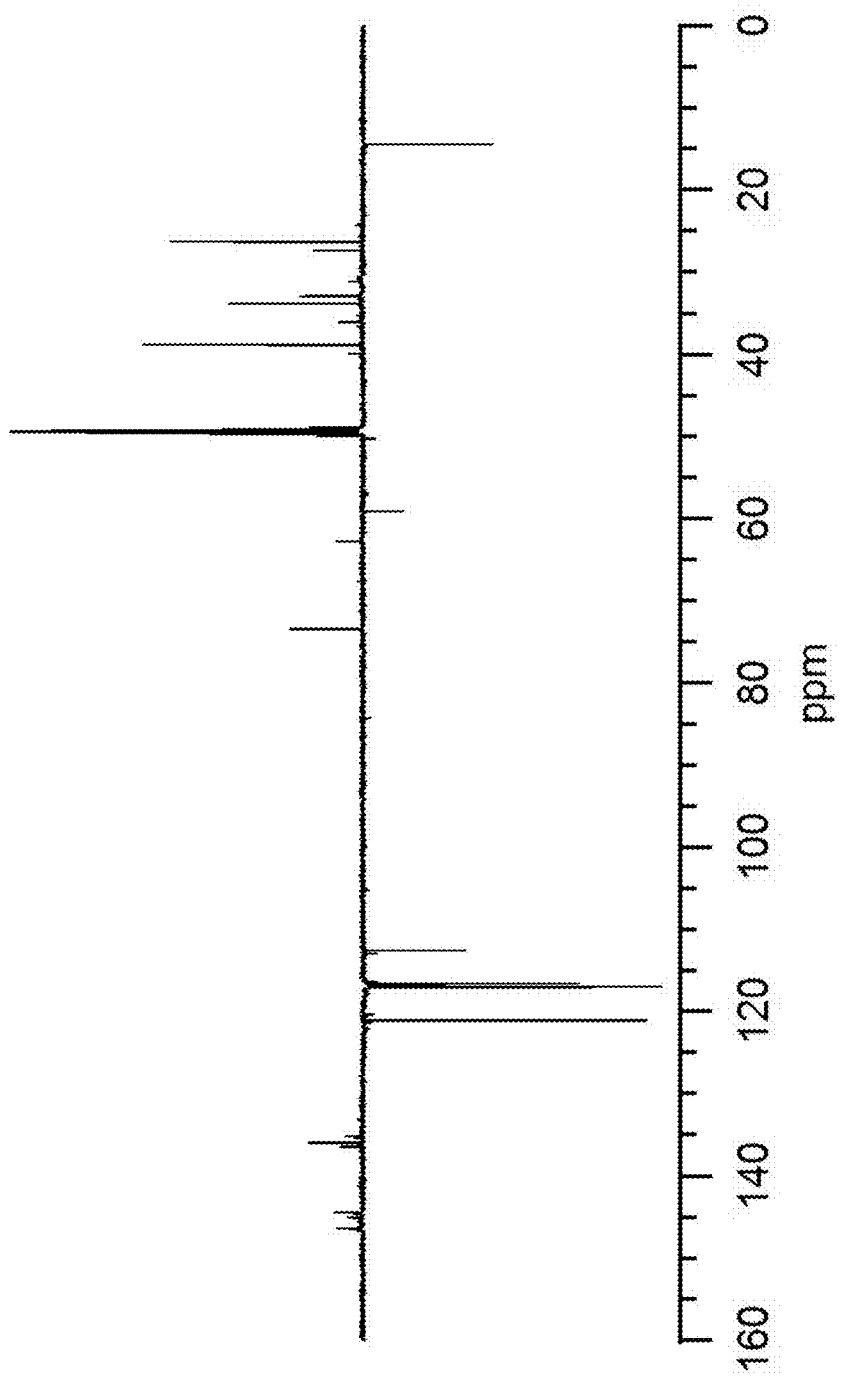
FIG. 22 is a $^{13}$C NMR spectrum depicting products of Column 2, Fractions 1-3.
Figure 23:
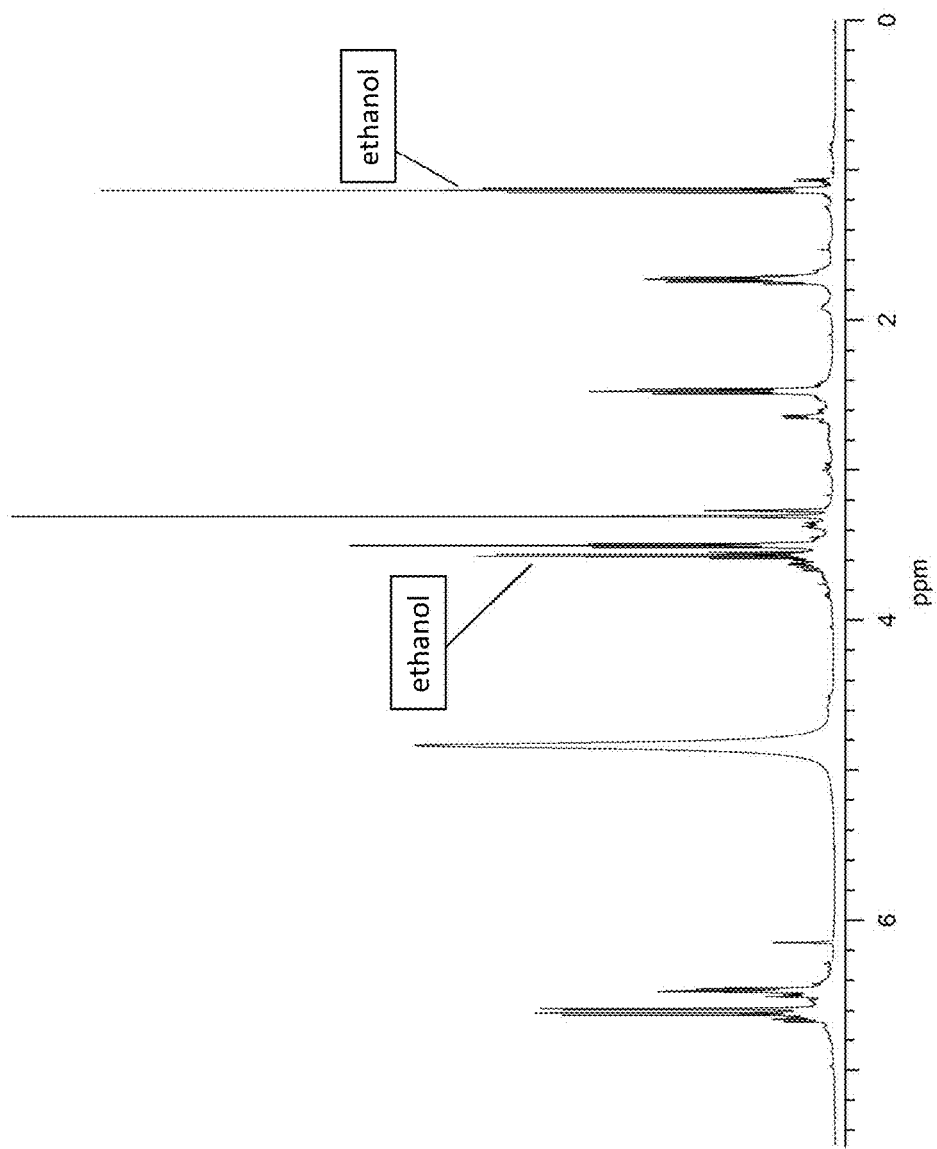
FIG. 23 is a $^1$H NMR spectrum depicting products of Column 2, Fractions 14-27.
Figure 24:
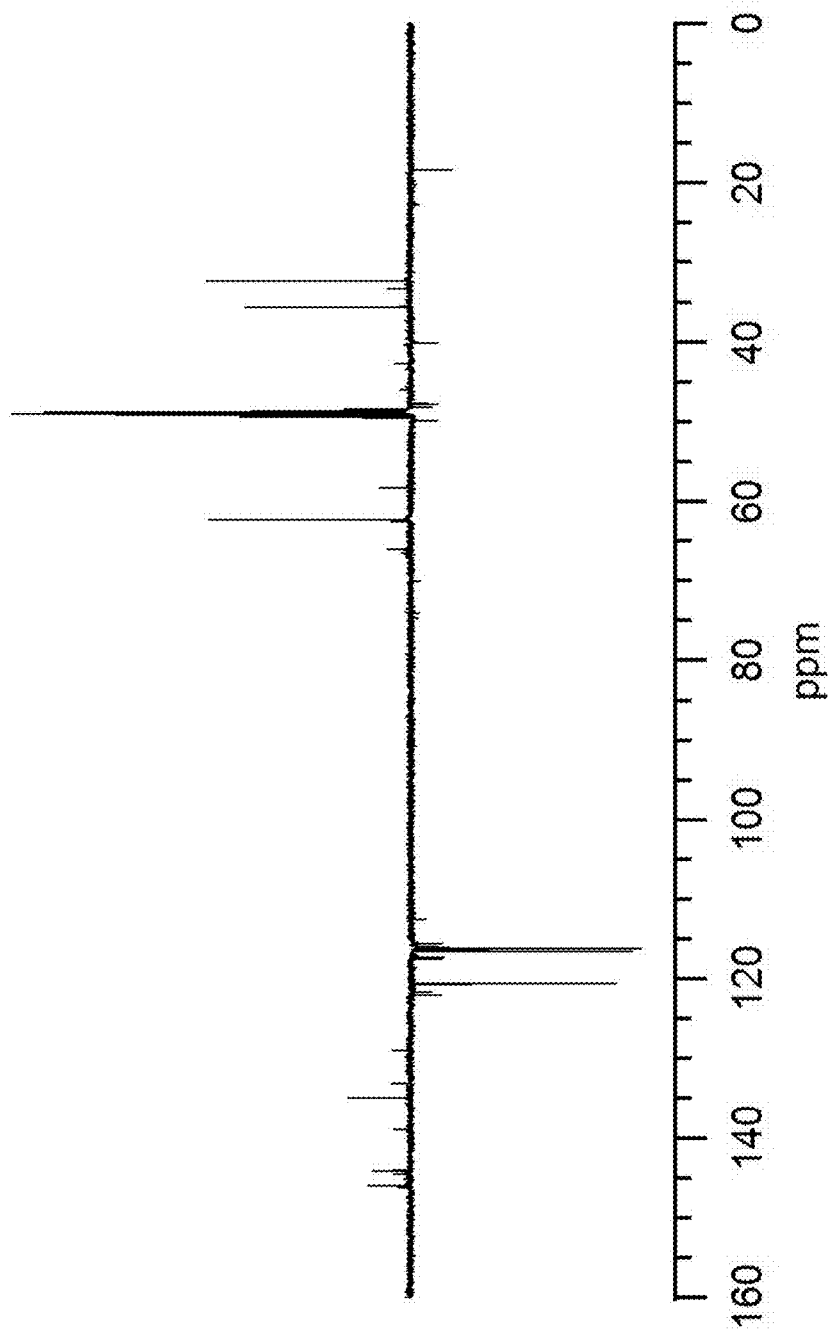
FIG. 24 is a $^{13}$C NMR APT spectrum depicting products of Column 2, Fractions 14-27.
Figure 25:
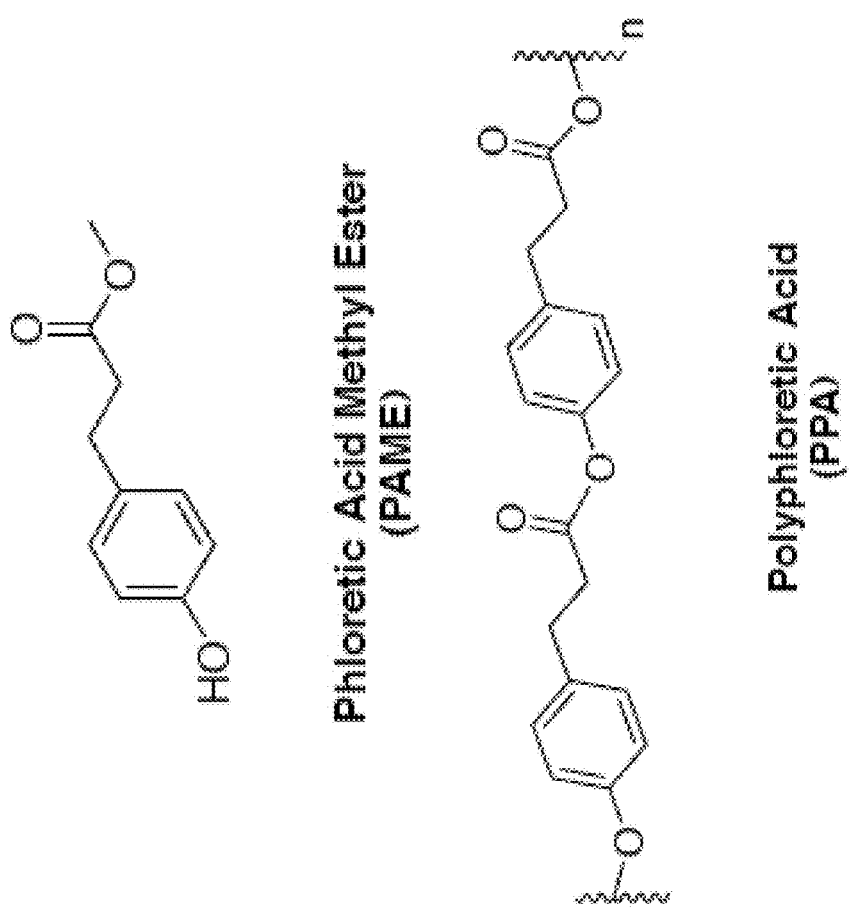
FIG. 25 depicts representative structures of the phloretic acid methyl ester (PAME) and the phloretic acid polymer, PPA.

The NMR spectra of the catalytic runs using $Cu_{20}PMO$ displayed only a few distinct signals different from signals identified in reactions under supercritical or control reactions under subcritical conditions. The product mixtures produced using $Cu_{20}PMO$ as the catalyst were clean and similar in terms of composition. 3 principal components (A-C) were assigned in the $^1H$ NMR spectra of product mixture (FIGS. 13 and 14). Main component A was identified as 4-propyl-catechol (Ozanne et al., 2003, Org. Lett. 5:2903-2906) and B as 4-(3-hydroxypropyl)-catechol (Bernini et al., 2012, J. Agric. Food Chem. 60:7408-7416). MS measurement confirmed these proposed structures, with observed masses of 151.18 g/mol and 168.11 g/mol, respectively. 2D NMR experiments, in addition to various $^{13}C$ NMR experiments, supported these structural assignments. The structure of component C has not been confirmed, however the structure is proposed to be 2,3-dihydro-1H-indene-5,6-diolor its isomer. Further, some reaction mixtures contain an additional compound, D, which is proposed to be 4-(3-methoxypropyl)catechol or its isomer; this structural assignment is supported by obtained MS data (181.11 g/mol). The ratio of these components was observed to vary depending on the reaction conditions used. A comparison is given in Table 10.

TABLE 10

Product ratios based on $^1$HNMR

| Entry | m (lignin3) [g] | m (PMO*) [g] | T [° C.] | m (crude) [g] | Ratio** A:B:C:D |
|---|---|---|---|---|---|
| Table 9. Entry 3 | 1 | 0.5 | 180 | 0.712 | 1:0.78:0.43:0.29 |
| Table 9. Entry 4 | 5 | 3 | 180 | 2.48 | 1:0.74:0.33:0.21 |
| Table 9. Entry 5 | 2 | 1 | 140 | 0.909 | 1:3.23:0.31:ND*** |
| Table 9. Entry 6 | 4 | 1 | 180 | 1.656 | 1:0.94:0.52:0.29 |

*catalyst $Cu_{20}PMO$,
**Ratio based on integration of signals in the $^1$HNMR spectra,
***ND = not determined.

Although not wishing to be bound by any particular theory, these compounds may be formed through a series of reactions involving depolymerization of lignin first via hydrogenolysis of the beta-O-4 linkage and subsequent hydrogenolysis, dehydration, and hydrogenation of the obtained intermediates (provided that the starting lignin structure is sufficiently regular). Traces of higher molecular weight components were observed in the GPC trace of the obtained product mixture, in addition to smaller signals in the NMR spectra, consistent with those observed in other product mixtures derived from biomass. However, the presence of the sharper signals suggested that only a few main components dominated the product mixture.

Isolation of Main Components by Column Chromatography

In order to obtain pure aromatic compounds, the main reaction components A through C were isolated by column chromatography. To the best of knowledge, this method has not yet been used to treat products of biomass disassembly. TLC experiments identified three main product spots when a $CH_3Cl$:methanol (3:1) mixture was used as eluent.

A total 0.350 g of crude product [the crude product originated from a catalytic run using 1 g lignin, 0.5 g catalyst, at 180° C. (Table 6, Entry 3)] was subjected to column chromatography. (Table 7, Col. 1) A $CH_3Cl$/methanol (20:1) eluent was used first, and was gradually changed to a more polar mixture (3:1 $CH_3Cl$/methanol) after the first two components were eluted. The first set of fractions yielded 30.20 mg, 31.7 mg and 29.8 mg brownish oil respectively (total yield 97.7 mg). $^1H$ NMR measurement confirmed that each fraction contained 4-propyl-catechol (A), 4-(3-methoxy-propyl)-catechol (C), and 4-(3-hydroxy-propyl)-catechol (B). 4-propyl-catechol (A) was the main component in these mixtures, although its amount varied within each fraction relative to the other components, and was most prevalent in the first fraction. The next set of fractions yielded 177.5 mg of a white solid that slowly turned beige over time. This white solid was identified as consisting primarily of 4-(3-hydroxypropyl)-catechol (B). The last set of fractions yielded 8.8 mg of product. This product is hypothesized to consist of oligomeric lignin fragments, as suggested by $^1H$ NMR spectra.

Attempts at column chromatography were repeated with a crude product batch weighing 0.5338 g (Table 7, Col. 2). The first set of fractions yielded 95.3 mg, 174.7 mg and 91.4 mg (total yield 361.4 mg) brownish oil respectively. NMR measurement confirmed that these contained components A, B, C, and D. The next set of fractions were found to contain 131.2 mg 4-(3-hydroxypropyl)-catechol. The last fractions yielded 43.3 mg of a product, and were hypothesized to contain oligomeric lignin fragments.

0.908 g of a different crude product mixture (obtained at 140° C.) was also subjected to column chromatography. This crude product provided 67.8 mg, 101.15 mg and 34.2 mg of mixed fractions mainly containing 4-propylcatechol (203.5 mg total yield). The next main fraction consisted of 433.1 mg 4-hydroxypropylcatechol. The remaining fractions consisted of 180.50 mg decomposition or oligomeric products. A summary of all the column chromatography experiments is given in Table 11. A more detailed summary is given in Table 1.

TABLE 11

Comparison of Different Column Chromatography Experiments and Amounts of the Obtained Aromatics

| Entry | Lignin (g) | Crude (g) | Crude product applied to column (g)) | Products A, C, and D (mg)) | Product B (mg) | Decomposition products or oligomers (mg) |
|---|---|---|---|---|---|---|
| Col. 1 | 1 | 0.712 | 0.350 | 97.70 | 177.5 | 8.8 |
| Col. 2 | 1 | 0.534 | 0.534 | 361.4 | 131.2 | 43.3 |
| Col. 3 | 2 | 0.908 | 0.908 | 203.5 | 433.1 | 180.5 |

TABLE 12

Fractionation of Lignin 2 to lighter and heavier components

| Entry | Lignin 2 (g) | Solids-Lignin 4 (g) | Yield (solids) % | Filtrate (Lignin 3) (g)* |
|---|---|---|---|---|
| 1 | 7.295 | 2.851 | 39.0 | 4.976 |
| 2 | 16.393 | 6.634 | 40.5 | 11.70 |
| 3 | 20.00 | 7.192 | 36.0 | 14.3 |
|  |  | Average yield : | 38.5 |  |

*the filtrate contained a small amount of EtAc, even after prolonged drying.

Isolation and Fractionation of Lignin

An efficient method for the isolation and fractionation of candlenut lignin is described herein. The heavier fraction was successfully depolymerized over a variety of porous metal oxide catalysts. Full biomass conversion and a high yield of bio-oil could be achieved with a reaction time of 6 hours using the $Cu_{20}La_{10}PMO$ catalyst. The average molecular weight of the product mixtures was within the desired 300 g/mol and 500 g/mol range. The non-copper containing catalysts also successfully converted Lignin 4 into smaller units, and the average molecular weight of the product mixtures was found to increase with reaction time. Although not wishing to be bound by any particular theory, the non-copper containing catalysts likely promoted base catalyzed degradation of lignin. It was observed that the copper and non-copper containing catalysts behave in a markedly different ways in reactions under sub-critical conditions with added hydrogen gas, with the non-copper catalysts leading to char formation and low biomass conversion. However, when $Cu_{20}PMO$ was used, a product mixture was obtained with a well-defined average molecular weight and low polydispersity. Improved biomass conversion and liquid phase product yield were observed through the manipulation of the product conditions. More detailed product analysis revealed that the obtained product is a mixture of distinct aromatic compounds. The results described herein demonstrate that the depolymerization reaction can proceed outside of supercritical reaction conditions. The results described herein also demonstrate that overreduction of aromatics can be avoided while significant yields of pure aromatic compounds can be obtained.

Example 2: Extraction and Depolymerization of Corn Lignin

PMO catalysts can be prepared based upon previously described procedures for synthesis of hydrotalcite-like materials (Hansen, et al., 2012, Green Chem. 14:2457-2461) using $Al^{3+}$ and $Mg^{2+}$ as salt hydrates. Variants can be synthesized by partial substitutions of the $Al^{3+}$ and $Mg^{2+}$ components with other $M^{3+}$ (La, Cr) or $M^{2+}$ (Cu, Mn, Zn) species. These hydrotalcite-like materials can then be converted to PMOs by calcining for 24 h at 460° C.

Example of Cu-Doped PMO Preparation

To a 3.0 L 3-neck flask outfitted with a mechanical stirrer and an addition funnel in a heat bath at 50-60° C., 8.47 g (0.08 mol) of $Na_2CO_3$ and 600 ml of DI water were combined. A mixture of $Al(NO_3)_3 \cdot 9H_2O$ (37.51 g, 0.1 mol), $Cu(NO_3)_2 \cdot 2.5H_2O$ (13.9 g, 0.06 mol), and $Mg(NO_3)_2 \cdot 6H_2O$ (61.4 g, 0.24 mol) in 480 ml of DI water was added dropwise with vigorous stirring, all the while keeping the pH of the solution near 10 by adjustment with alternating solutions of aqueous 1.0 N $Na_2CO_3$. Following addition, the solution is allowed to stir overnight at 55° C. The next day, the blue precipitate that formed in the reaction vessel was filtered, and the filter cake was further washed with 1.0 L DI water. This solid was then dried in oven at 100° C. overnight to give 58.6 g of blue hydrotalcite-like material. This material was then heated at 460° C. overnight to give 19.6 g of dark green PMO. This material was used as is in the next reaction.

Preparing Organic-Extracted Lignin 842 g of pretreated and enzymatically hydrolyzed corn stover as a ~70% wet solid by wt. was placed in a 3000 ml, 3-neck flask and combined with 1.0 L ethyl acetate. This material was then refluxed overnight in a heat bath set to 84° C. The ethyl acetate insoluble lignin was then removed with filtration and the filtrate was concentrated to give 260.7 g of crude solid that still contained water. A sample was dried at 100° C. overnight to determine total dry weight, which was calculated to be ~78.2 g. The wet crude solid was taken on as is in the next reaction.

Lignin Depolymerization

Catalytic Depolymerization of Corn Lignin to Obtain PAME with PMO 14.0 g of crude, wet corn lignin obtained from ethyl acetate extraction was combined with 7.0 g of Cu-doped PMO catalyst and 400 ml of methanol in a 2.0 L Parr high pressure reactor. The reaction vessel was heated at 140° C. under 1000 psi $H_2$ pressure with vigorous stirring for 14 hours. The reaction was then brought to ambient pressure and temperature and the material was filtered to remove solid. The light brown filtrate was then concentrated to give 15.9 g of a crude brown amorphous solid. $^1H$ NMR shows PAME as the main lignin monomer, as well as the presence of carbohydrate and fatty acid.

Catalytic Depolymerization of Corn Lignin to Obtain PAME with Copper Chromite 8.0 g of crude, wet corn lignin obtained from ethyl acetate extraction was combined with 4.0 g of copper chromite and 400 ml of methanol in a 2.0 L Parr high pressure reactor. The reaction vessel was heated at 140° C. under 1000 psi $H_2$ pressure with vigorous stirring for 12 hours. The reaction was then brought to ambient pressure and temperature and the material was filtered to remove solid. The light brown filtrate was then concentrated to give 7.0 g of a crude brown amorphous solid. ¹H NMR shows PAME and p-coumaric methyl ester as the two main lignin monomers, as well as the presence of carbohydrate and fatty acid. It can be seen that the use of copper chromite results in a less clean conversion to phloretic acid as compared to the use of PMO catalysts, but product is still observed.

Characterization of Crude Products and Identification of PAME

Figure 26:
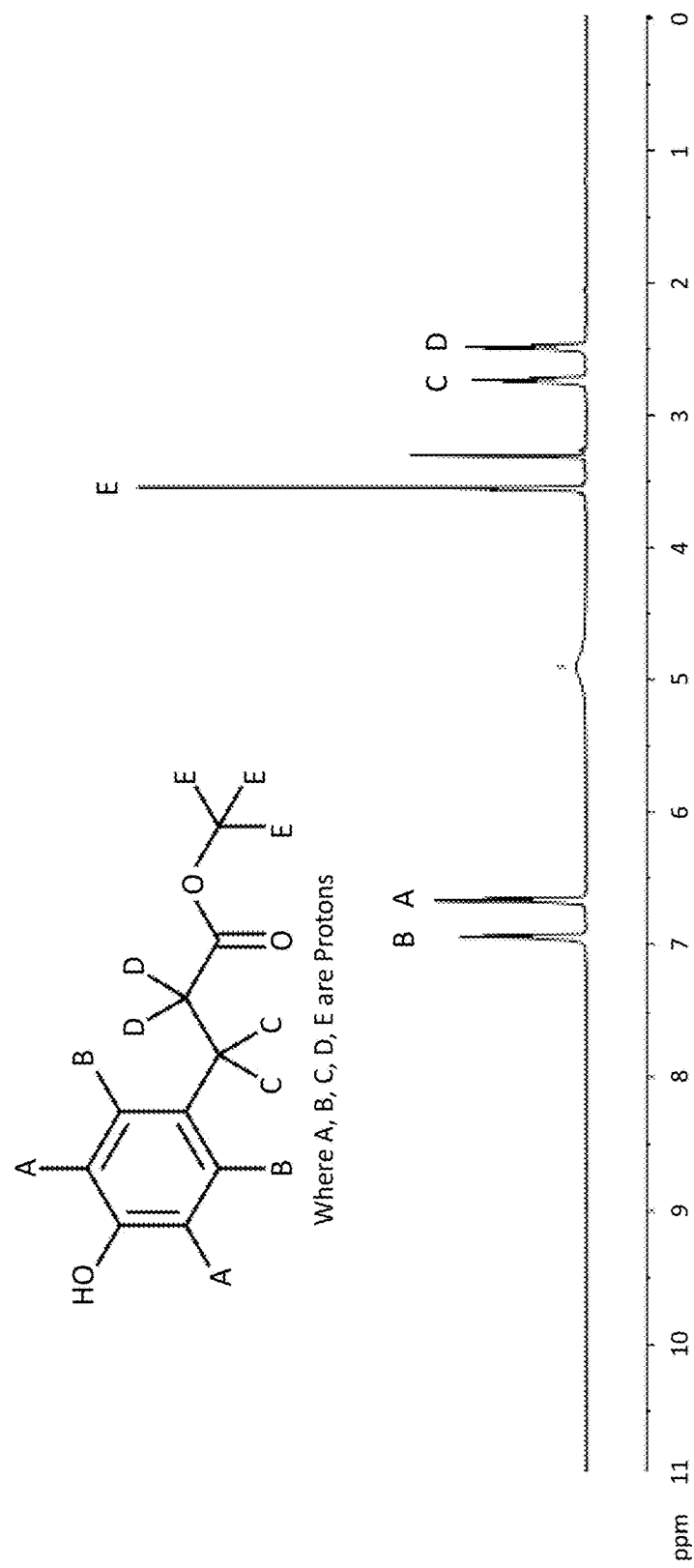
FIG. 26 is a $^1$H NMR spectrum depicting the phloretic acid methyl ester (PAME) standard in $CD_3OD$.
Figure 27:
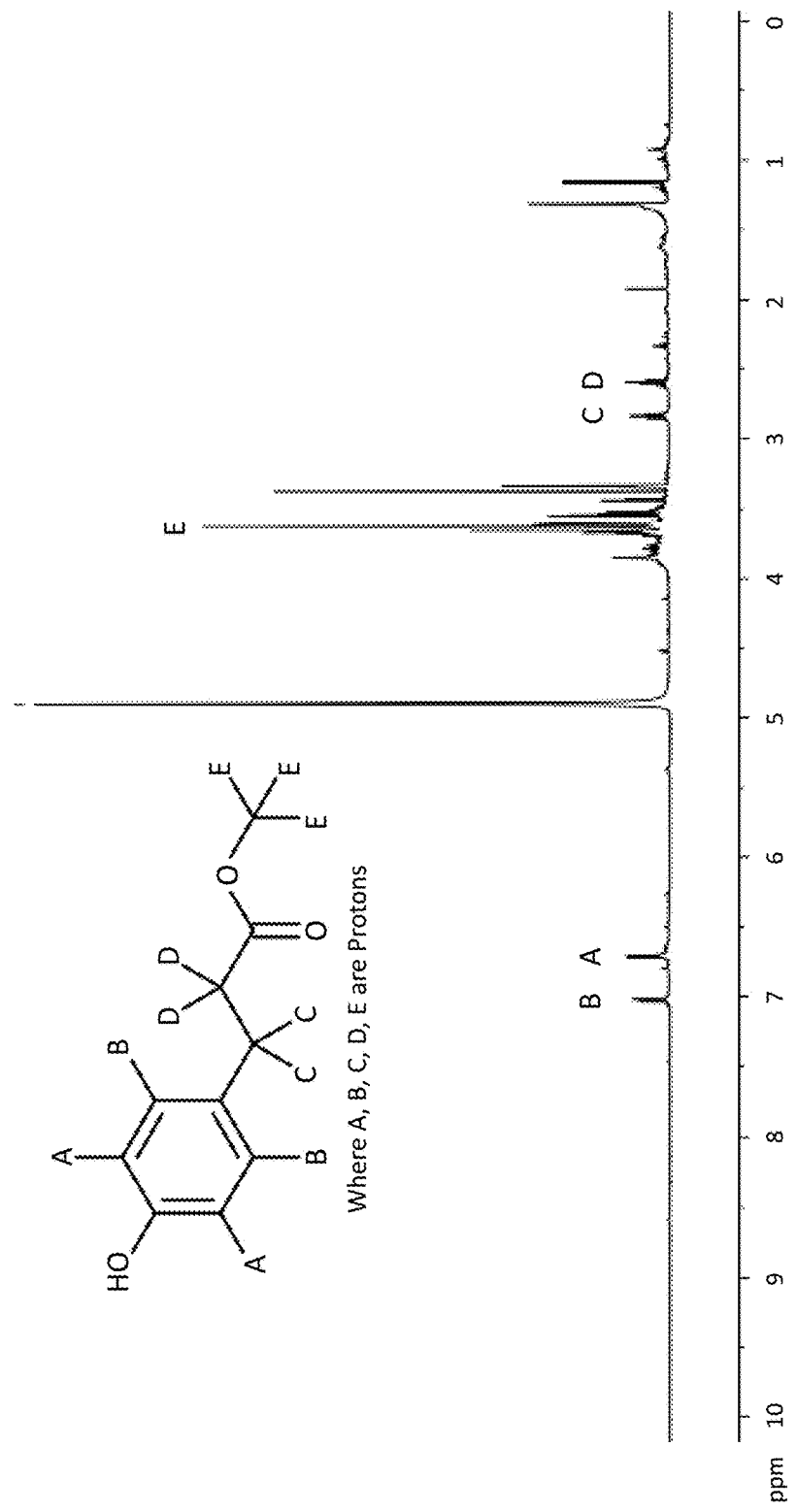
FIG. 27 is a $^1$H NMR spectrum depicting the crude depolymerization product from corn lignin using Cu-doped copper catalyst (in $CD_3OD$).
Figure 28:
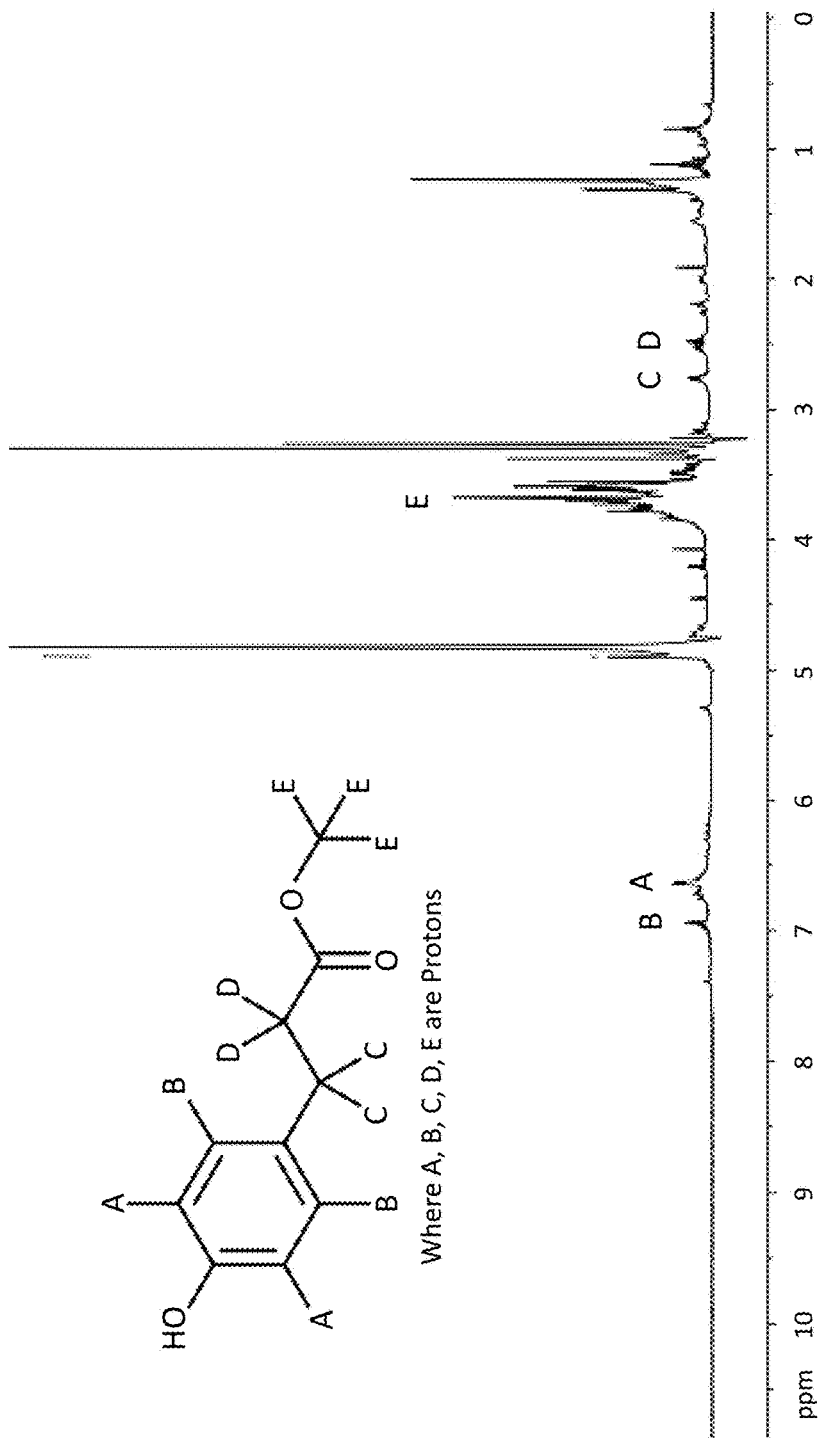
FIG. 28 is a $^1$H NMR spectrum depicting the crude depolymerization product from corn lignin using copper chromite catalyst (in $CD_3OD$).
Figure 29:
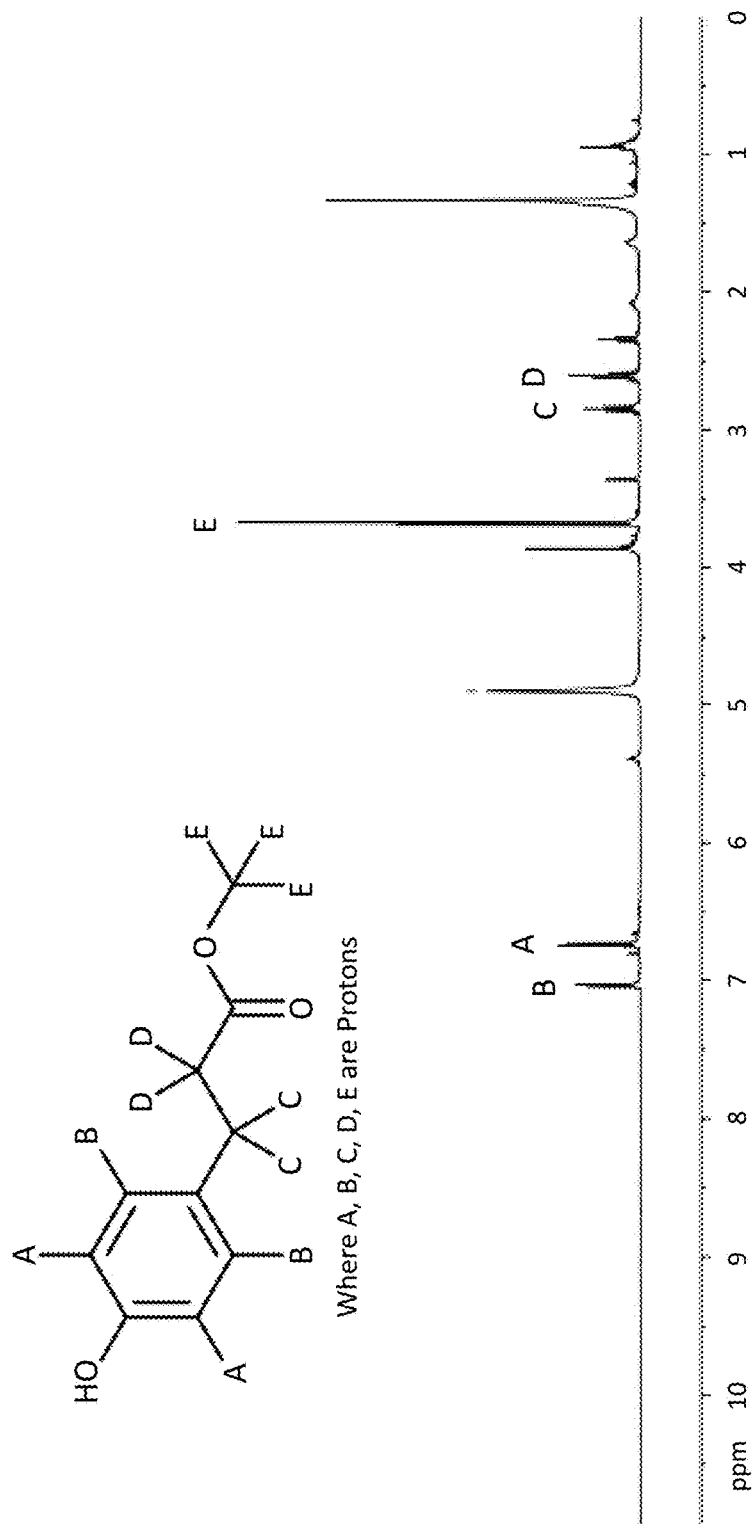
FIG. 29 is a $^1$H NMR spectrum depicting the crude depolymerization product from corn lignin using Cu-doped copper catalyst after washing and extraction to remove carbohydrates and inorganic material (in $CD_3OD$). The product is the crude depolymerization product depicted in FIG. 28 further purified by dissolving the crude product in ethyl acetate, washing the organic phase with water twice, concentrating the organic phase, and again extracting the residual crude phase with diethyl ether and then removing the ether. The other major product in the sample is assigned as fatty acid.
Figure 30:
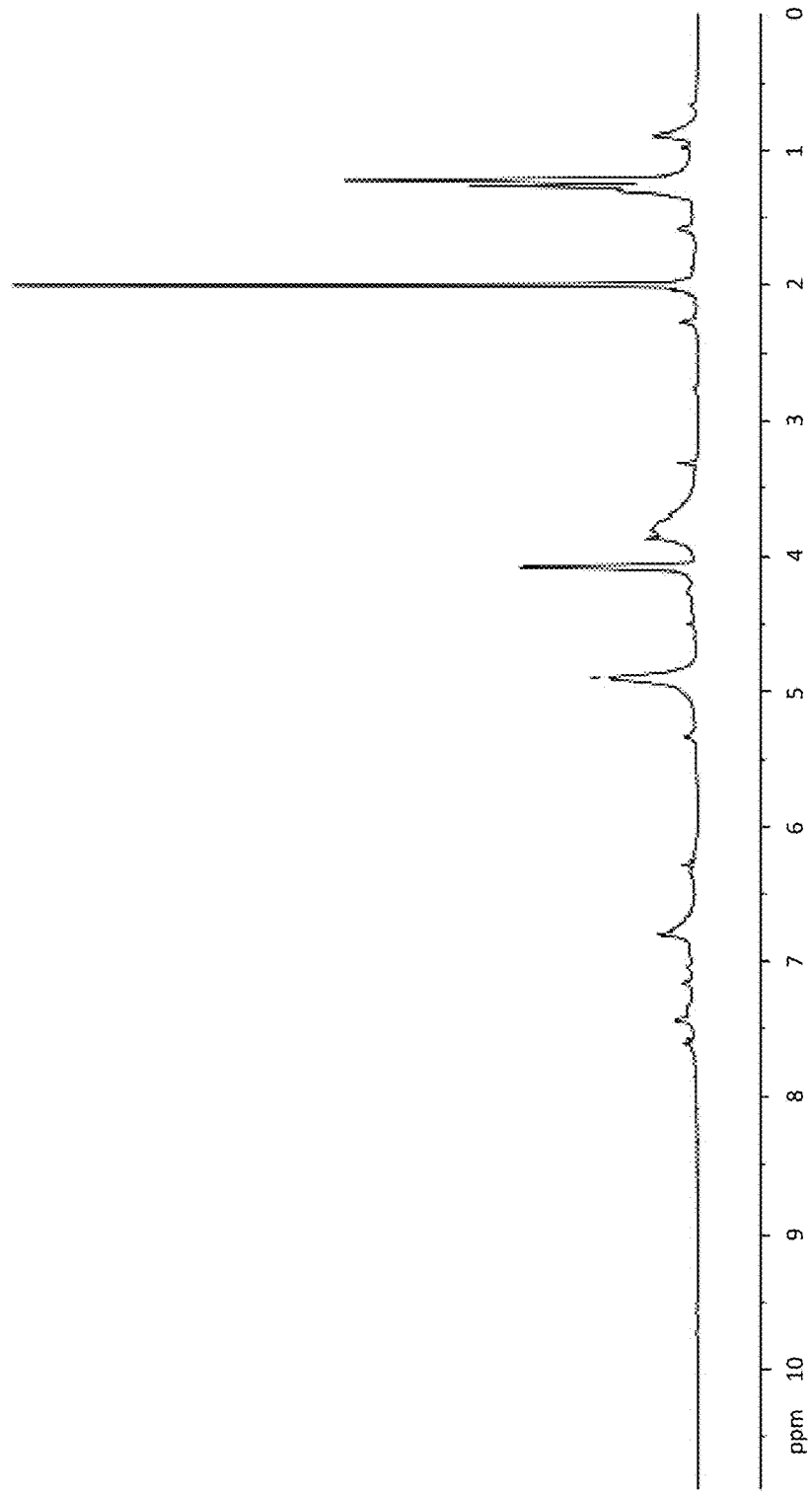
FIG. 30 is a $^1$H NMR spectrum depicting the crude lignin starting material obtained from the ethyl acetate extraction of corn stover.

¹H NMR was used to characterize the crude products and determine the presence of PAME. A representative ¹H NMR spectrum of a PAME standard can be found in FIG. 26. A representative ¹H NMR spectrum of a representative depolymerization product from crude corn lignin using Cu-doped PMO can be found in FIG. 27. A representative ¹H NMR of a representative depolymerization product from crude corn lignin using copper chromite can be found in FIG. 28. The crude depolymerization product was also further purified by dissolving the crude product in ethyl acetate, washing the organic phase with water twice, concentrating the organic phase, and again extracting the residual crude phase with diethyl ether and then removing the ether. A representative ¹H NMR spectrum of this material can be found in FIG. 29. A representative ¹H NMR spectrum of the crude lignin starting material obtained from the extraction of corn stover can be found in FIG. 30.

Figure 31:
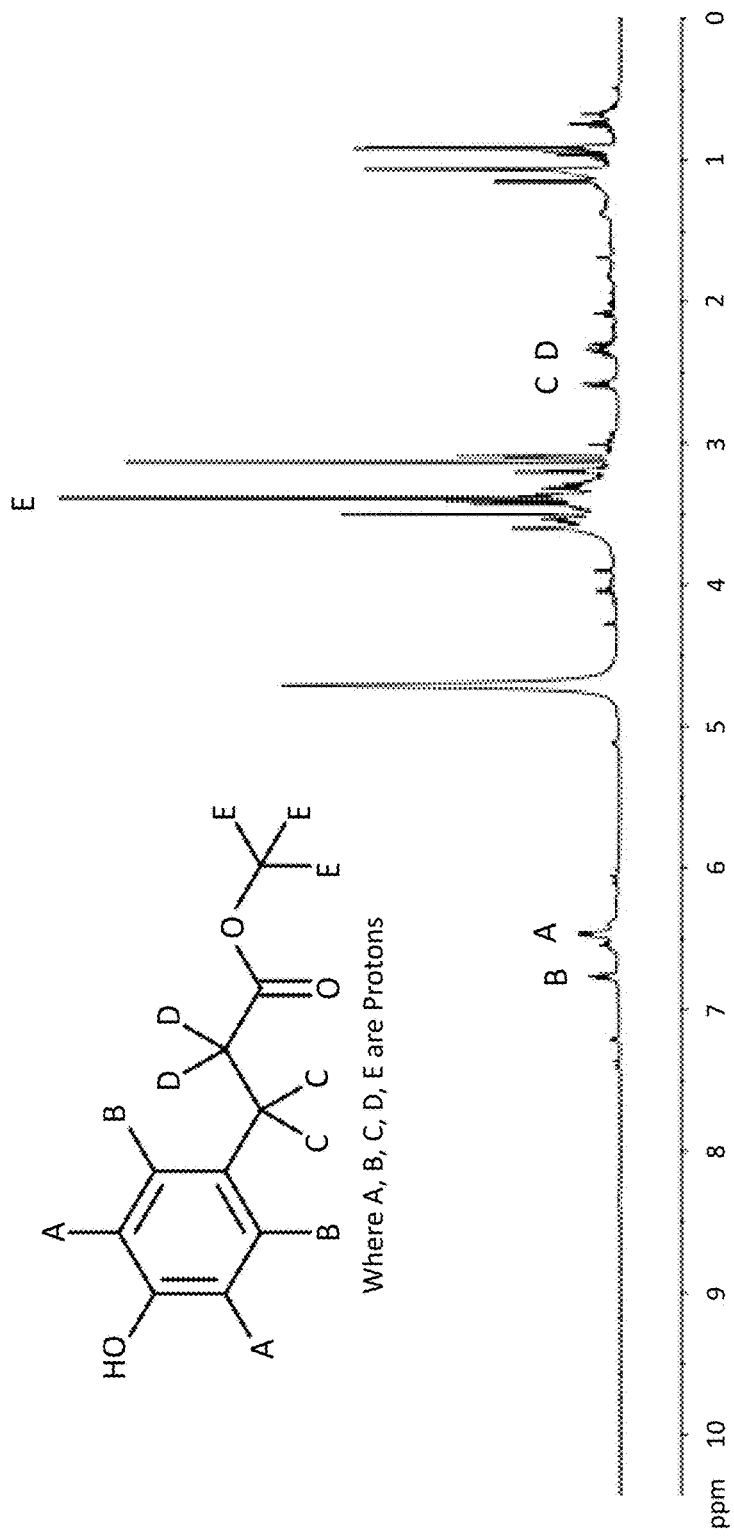
FIG. 31 is a $^1$H NMR of the crude depolymerization product from corn lignin using $Cu_3(OH)CO_3$/Alumina as catalyst (in $CD_3OD$).

Example 3: Depolymerization of Corn Lignin Using Cu₃(OH)CO₃/Alumina as Catalyst 12 g (calculated) of organosolv corn stover lignin, prepared as described in Example 2 (Preparing Organic-Extracted Lignin), was combined with 3 g of basic alumina oxide and 4 g Cu₃(OH)CO₃ in 400 ml of methanol. The reaction mixture was put under 1000 psi of H₂ pressure at 140° C. and vigorously stirred for 12 hours. The reaction mixture was then brought to ambient temperature and pressure, and was filtered to remove solid. The filtrate was then concentrated to give 12 g of product material. A ¹H NMR of the product material is shown in FIG. 31. The product material contains significant amounts of phloretic acid methyl ester, as well as the corresponding p-coumaryl methyl ester analog.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method for producing a monomer from a biopolymer source, the method comprising depolymerizing at least one biopolymer from the biopolymer source into a monomer within a system comprising at least one solvent and a porous metal oxide (PMO) catalyst, wherein the system is heated to a temperature no greater than about 220° C.

2. The method of claim 1, wherein the method further comprises the step of extracting the at least one biopolymer from the biopolymer source.

3. The method of claim 2, wherein the method further comprises the step of fractionating the at least one biopolymer from the biopolymer source.

4. The method of claim 1, wherein the at least one biopolymer is lignin.

5. The method of claim 1, wherein the PMO catalyst comprises at least one divalent metal cation and at least one trivalent metal cation.

6. The method of claim 5, wherein the at least one divalent metal cation is selected from the group consisting of copper (II), magnesium(II), manganese(II), and zinc(II) and the at least one trivalent metal cation is selected from the group consisting of aluminum(III), chromium(III), and lanthanum (III).

7. The method of claim 5, wherein the molar ratio of total divalent metal cations to total trivalent metal cations is about 3:1.

8. The method of claim 1, wherein the system is pressurized by the addition of a gas to the system.

9. A method for producing a monomer from corn biomass, the method comprising depolymerizing corn lignin from the corn biomass into a phloretic acid derivative within a system comprising at least one solvent and a porous metal oxide (PMO) catalyst; wherein the system is heated to a temperature from about 120° C. to about 200° C.

10. The method of claim 9, wherein the at least one solvent is methanol.

11. The method of claim 9, wherein the PMO catalyst is supported on a catalyst support selected from the group consisting of alumina, basic aluminum oxide, barium sulfate, carbon, calcium carbonate, silica, titania, zirconia, and any combinations thereof.

12. The method of claim 9, wherein the PMO catalyst has a catalyst loading from about 0.05 weight percent to about 60 weight percent.

* * * * *